(12) United States Patent
Zheng

(10) Patent No.: US 8,278,412 B2
(45) Date of Patent: Oct. 2, 2012

(54) POLYPEPTIDE, NUCLEIC ACID MOLECULE ENCODING IT AND THEIR USES

(75) Inventor: Hong Zheng, Hubei (CN)

(73) Assignee: Hong Zheng, Hubei (CN)

( * ) Notice: Subject to any disclaimer, the term of this patent is extended or adjusted under 35 U.S.C. 154(b) by 382 days.

(21) Appl. No.: 12/373,048

(22) PCT Filed: Jul. 10, 2007

(86) PCT No.: PCT/CN2007/002111
§ 371 (c)(1),
(2), (4) Date: Jan. 8, 2009

(87) PCT Pub. No.: WO2008/009214
PCT Pub. Date: Jan. 24, 2008

(65) Prior Publication Data
US 2009/0291441 A1 Nov. 26, 2009

(30) Foreign Application Priority Data
Jul. 10, 2006 (CN) .......................... 2006 1 0098727

(51) Int. Cl.
*A61K 38/00* (2006.01)
*A61K 39/00* (2006.01)
*C07K 14/00* (2006.01)
*C07K 2/00* (2006.01)

(52) U.S. Cl. ........ 530/300; 530/324; 530/326; 530/350; 424/184.1; 424/185.1; 424/277.1

(58) Field of Classification Search .................. None
See application file for complete search history.

(56) References Cited

FOREIGN PATENT DOCUMENTS
WO  WO 2004/050860 A2 * 6/2004
WO  WO2006/028655    3/2006

OTHER PUBLICATIONS zymogen granule protein 16 homolog B precursor (NCBI Ref. Seq. NP_660295, May 4, 2006).*
Tanaka et al. (1985 Proc. Natl. Acad. Sci USA 82:3400-3404).*
Harlow and Lane (Antibodies: A Laboratory Manual, Cold Spring Harbor Laboratory, Cold Spring Harbor, NY, 1988, p. 76).*
Greenspan et al. (Nature Biotechnology 7:936-937 (1999)).*
Harlow and Lane (Antibodies, a Laboratory Manual, Cold Spring Harbor Laboratory Press, 1988, pp. 72-76 and 141-142).*
Clark, H.F., et al, "The Secreted Protein Discovery Initiative (SkPDI), A Large-Scale Effort to Identify Novel Human Secreted and Transmembrane Proteins: A Bioinformatics Assessment", Genome Res. Sep. 15, 2003, vol. 13, No. 10, pp. 2265-2270.
Genbank accession No. AAQ89380, Oct. 3, 2003.
Genbank accession No. Ay359021, Oct. 3, 2003.

* cited by examiner

*Primary Examiner* — Peter J Reddig
(74) *Attorney, Agent, or Firm* — Occhiuti Rohlicek & Tsao LLP

(57) ABSTRACT

A polypeptide containing epitope of the amino acid sequence shown in SEQ ID NO:3 is provided, which is selected from the amino acid sequence of SEQ ID NO:3 and amino acids at 16-32 positions, amino acids at 1-30 positions, amino acids at 50-80 positions and amino acids at 17-200 positions of the amino acid sequence shown in SEQ ID NO:3. The nucleic acid molecule encoding the polypeptide, recombinant vectors and host cells comprising the nucleic acid molecule are also provided. The polypeptide and the nucleic acid molecule encoding it can be used for preparing reagents, kits or devices for diagnosing the diseases characterized by EECP expression and pharmaceutical compositions for preventing or treating the diseases characterized by EECP expression by increasing or inhibiting EECP expression and/or activity.

15 Claims, 9 Drawing Sheets

| | |
|---|---|
| 1 | tcgcttcttccttctgg |
| 18 | atgggggcccaggggggcccaggagagtataaaggcgatgtggagg |
| 63 | gtgcccggcacaaccagacgcccagtcacaggcgagagccctggg |
| 108 | atgcaccggccagaggccatgctgctgctgctcacgcttgccctc |
| 153 | ctggggggccccacctgggcagggaagatgtatggccctggagga |
| 198 | ggcaagtatttcagcaccactgaagactacgaccatgaaatcaca |
| 243 | gggctgtgggtgtctgtaggtcttctcctggtgaaaagtgtccag |
| 288 | gtgaaacttggagactcctgggacgtgaaactgggagccttaggt |
| 333 | gggaatacccaggaagtcaccctgcagccaggcgaatacatcaca |
| 378 | aaagtctttgtcgccttccaagctttcctccggggtatggtcatg |
| 423 | tacaccagcaaggaccgctatttctatttgggaagcttgatggc |
| 468 | cagatctcctctgcctaccccagccaagagggggcaggtgctggtg |
| 513 | ggcatctatggccagtatcaactccttggcatcaagagcattggc |
| 558 | tttgaatggaattatccactagaggagccgaccactgagccacca |
| 603 | gttaatctcacatactcagcaaactcacccgtgggtcgctagggt |
| 648 | ggggtatggggccatccgagctgaggccatctgtgtggtggtggc |
| 693 | tgatagtactggagtaactgagtcgggacgctgaatctgaatcca |
| 738 | ccaataaataaagcttctgcagaatcagtgt |

SEQ ID NO:1

| | |
|---|---|
| 18 | atgggggcccaggggggcccaggagagtataaaggcgatgtggagg |
| 63 | gtgcccggcacaaccagacgcccagtcacaggcgagagccctggg |

SEQ ID NO:2

Figure 1 amino acid sequence composing EECP

| | | | | | | | | | | | | | | |
|---|---|---|---|---|---|---|---|---|---|---|---|---|---|---|
| M | G | A | Q | G | A | Q | E | S | I | K | A | M | W | R | 15 |
| V | P | G | T | T | R | R | P | V | T | G | E | S | P | G | 30 |
| M | H | R | P | E | A | M | L | L | L | T | L | A | L | 45 |
| L | G | G | P | T | W | A | G | K | M | Y | G | P | G | G | 60 |
| G | K | Y | F | S | T | T | E | D | Y | D | H | E | I | T | 75 |
| G | L | R | V | S | V | G | L | L | L | V | K | S | V | Q | 90 |
| V | K | L | G | D | S | W | D | V | K | L | G | A | L | G | 105 |
| G | N | T | Q | E | V | T | L | Q | P | G | E | Y | I | T | 120 |
| K | V | F | V | A | F | Q | A | F | L | R | G | M | V | M | 135 |
| Y | T | S | K | D | R | Y | F | Y | F | G | K | L | D | G | 150 |
| Q | I | S | S | A | Y | P | S | Q | E | G | Q | V | L | V | 165 |
| G | I | Y | G | Q | Y | Q | L | L | G | I | K | S | I | G | 180 |
| F | E | W | N | Y | P | L | E | E | P | T | T | E | P | P | 195 |
| V | N | L | T | Y | S | A | N | S | P | V | G | R | * | | 210 |

Met-Gly-Ala-Gln-Gly-Ala-Gln-Glu-Ser-Ile-Lys-Ala-Met-Trp-Arg-Val-Pro-Gly-Thr-Thr-Arg-
Arg-Pro-Val-Thr-Gly-Glu-Ser-Pro-Gly-Met-His-Arg-Pro-Glu-Ala-Met-Leu-Leu-Leu-Leu-Thr-
Leu-Ala-Leu-Leu-Gly-Gly-Pro-Thr-Trp-Ala-Gly-Lys-Met-Tyr-Gly-Pro-Gly-Gly-Lys-Tyr-
Phe-Ser-Thr-Thr-Glu-Asp-Tyr-Asp-His-Glu-Ile-Thr-Gly-Leu-Arg-Val-Ser-Val-Gly-Leu-Leu-
Leu-Val-Lys-Ser-Val-Gln-Val-Lys-Leu-Gly-Asp-Ser-Trp-Asp-Val-Lys-Leu-Gly-Ala-Leu-Gly-
Gly-Asn-Thr-Gln-Glu-Val-Thr-Leu-Gln-Pro-Gly-Glu-Tyr-Ile-Thr-Lys-Val-Phe-Val-Ala-Phe-
Gln-Ala-Phe-Leu-Arg-Gly-Met-Val-Met-Tyr-Thr-Ser-Lys-Asp-Arg-Tyr-Phe-Tyr-Phe-Gly-Lys-
Leu-Asp-Gly-Gln-Ile-Ser-Ser-Ala-Tyr-Pro-Ser-Gln-Glu-Gly-Gln-Val-Leu-Val-Gly-Ile-Tyr-Gly-
Gln-Tyr-Gln-Leu-Leu-Gly-Ile-Lys-Ser-Ile-Gly-Phe-Glu-Trp-Asn-Tyr-Pro-Leu-Glu-Glu-Pro-
Thr-Thr-Glu-Pro-Pro-Val-Asn-Leu-Thr-Tyr-Ser-Ala-Asn-Ser-Pro-Val-Gly-Arg *   SEQ ID NO:3

Met-Gly-Ala-Gln-Gly-Ala-Gln-Glu-Ser-Ile-Lys-Ala-Met-Trp-Arg-Val-Pro-Gly-Thr-Thr-Arg-
Arg-Pro-Val-Thr-Gly-Glu-Ser-Pro-Gly   SEQ ID NO:4

```
1                                    tcgcttcttccttctgg
18  atgggggggccaggggggcccaggagagtataaaggcgatgtggagg
    M  G  A  Q  G  A  Q  E  S  I  K  A  M  W  R    15
63  gtgcccggcacaaccagacgccaagtcacaggcgagagccctggg
    V  P  G  T  T  R  R  P  V  T  G  E  S  P  G    30
108 atgaaccggccagaggccatgctgctgctgctcacgcttgccctc
    M  N  R  P  E  A  M  L  L  L  L  T  L  A  L    45
153 ctgggggggccccacctgggcagggaagatgtatggccctggagga
    L  G  G  P  T  W  A  G  K  M  Y  G  P  G  G    60
198 ggcaagtatttcagcaccactgaagactacgaccatgaaatcaca
    G  K  Y  F  S  T  T  E  D  Y  D  H  E  I  T    75
243 ggctgcgggtgtctgtaggtcttctactggtgaaaagtgtccag
    G  L  R  V  S  V  G  L  L  L  V  K  S  V  Q    90
288 gtgaaacttggagactcctgggacgtgaaactgggagccttaggt
    V  K  L  G  D  S  W  D  V  K  L  G  A  L  G   105
333 gggaatacccaggaagtcaccctgcagccaggcgaatacatcaca
    G  N  T  Q  E  V  T  L  Q  P  G  E  Y  I  T   120
378 aaagtctttgtcgccttccaagcttttctcggggtatggtcatg
    K  V  F  V  A  F  Q  A  F  L  R  G  M  V  M   135
423 tacacccagcaaggaccgctatttctattttgggaagcttgatggc
    Y  T  S  K  D  R  Y  F  Y  F  G  K  L  D  G   150
468 cagatctcctctgcctaccccagccaagaggggcaggtgctggtg
    Q  I  S  S  A  Y  P  S  Q  E  G  Q  V  L  V   165
513 ggcatctatggccagtatcaactccttggcatcaagagcattgga
    G  I  Y  G  Q  Y  Q  L  L  G  I  K  S  I  G   180
558 tttgaatggaattatccactagaggagccgaccactgagccacca
    F  E  W  N  Y  P  L  E  E  P  T  T  E  P  P   195
603 gttaatctcacatactcagcaaactcacccgtgggtcgctagggt
    V  N  L  T  Y  S  A  N  S  P  V  G  R  *      210
648 ggggtatgggccatccgagctgaggccatctgtgtggtggtggc
693 tgatagtactggagtaactgagtcgggacgctgaatctgaatcca
738 ccaataaataaagcttctgcagaatcagtgt
```

SEQ ID NO:3 → (points to the protein sequence)

SEQ ID NO:1 (points to the nucleotide sequence)

B

Figure 3 cDNA nucleotide and amino acid sequence composing HRPE733

```
  1   atgcaccggccagaggccatgctgctgctgctcacgcttgccctc
 45   ctgggggcccacctgggcagggaagatgtatggccctggagga
 90   ggcaagtatttcagcaccactgaagactacgaccatgaaatcaca
135   gggctgcgggtgtctgtaggtcttctcctggtgaaaagtgtccag
180   gtgaaacttggagactcctgggacgtgaaactgggagccttaggt
225   gggaatacccaggaagtcaccctgcagccaggcgaatacatcaca
270   aaagtctttgtcgccttccaagctttcctccggggtatggtcatg
315   tacaccagcaaggaccgctatttctattttgggaagcttgatggc
360   cagatctcctctgcctaccccagccaagagggggcaggtgctggtg
405   ggcatatatggccagtatcaactccttggcatcaagagcattggc
450   tttgaatggaattatccactagaggagccgaccactgagccacca
495   gttaatctcacataotcagcaaactcaccggtgggtgctagggt
540   ggggtatggggccatccgagctgaggcatctgtgtggtggtggc
585   tgatagtactggagtaactgagtcgggacgctgaatctgaatcca
630   ccaataaataaagcttctgcagaatcagtgt
```
SEQ ID NO:5

-Met-His-Arg-Pro-Glu-Ala-Met-Leu-Leu-Leu-Leu-Thr-
Leu-Ala-Leu-Leu-Gly-Gly-Pro-Thr-Trp-Ala-Gly-Lys-Met-Tyr-Gly-Pro-Gly-Gly-Gly-Lys-Tyr-
Phe-Ser-Thr-Thr-Glu-Asp-Tyr-Asp-His-Glu-Ile-Thr-Gly-Leu-Arg-Val-Ser-Val-Gly-Leu-Leu-
Leu-Val-Lys-Ser-Val-Gln-Val-Lys-Leu-Gly-Asp-Ser-Trp-Asp-Val-Lys-Leu-Gly-Ala-Leu-Gly-
Gly-Asn-Thr-Gln-Glu-Val-Thr-Leu-Gln-Pro-Gly-Glu-Tyr-Ile-Thr-Lys-Val-Phe-Val-Ala-Phe-
Gln-Ala-Phe-Leu-Arg-Gly-Met-Val-Met-Tyr-Thr-Ser-Lys-Asp-Arg-Tyr-Phe-Tyr-Phe-Gly-Lys-
Leu-Asp-Gly-Gln-Ile-Ser-Ser-Ala-Tyr-Pro-Ser-Gln-Glu-Gly-Gln-Val-Leu-Val-Gly-Ile-Tyr-Gly-
Gln-Tyr-Gln-Leu-Leu-Gly-Ile-Lys-Ser-Ile-Gly-Phe-Glu-Trp-Asn-Tyr-Pro-Leu-Glu-Glu-Pro-
Thr-Thr-Glu-Pro-Pro-Val-Asn-Leu-Thr-Tyr-Ser-Ala-Asn-Ser-Pro-Val-Gly-Arg *

SEQ ID NO:6

Figure 4

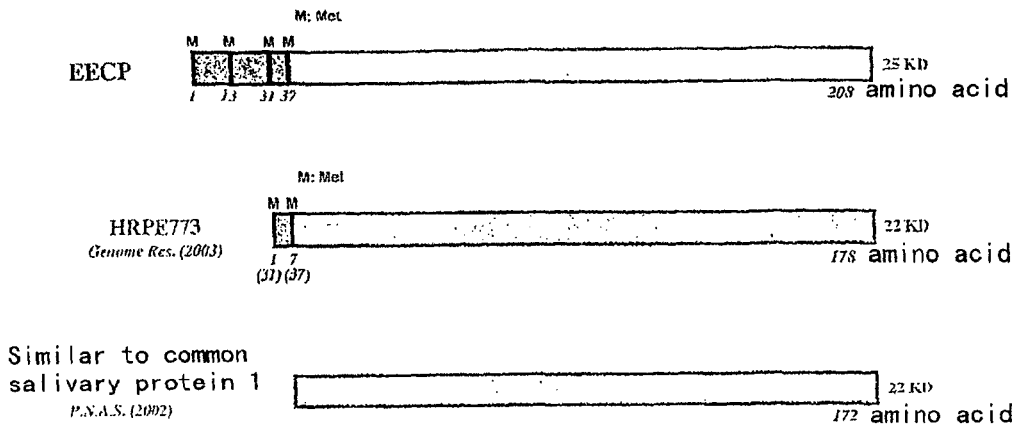
Figure 5
Western blotting analysis (antibody test)
media supernatant of cultured cells
(transfected and endogenous)
human plasma
(using EECP targeting antibody)
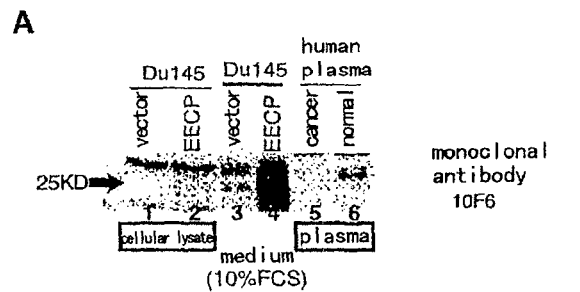
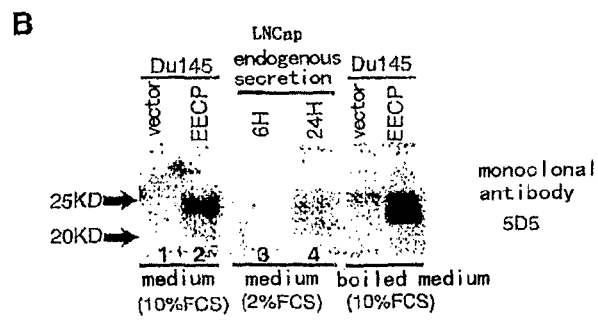
Figure 6

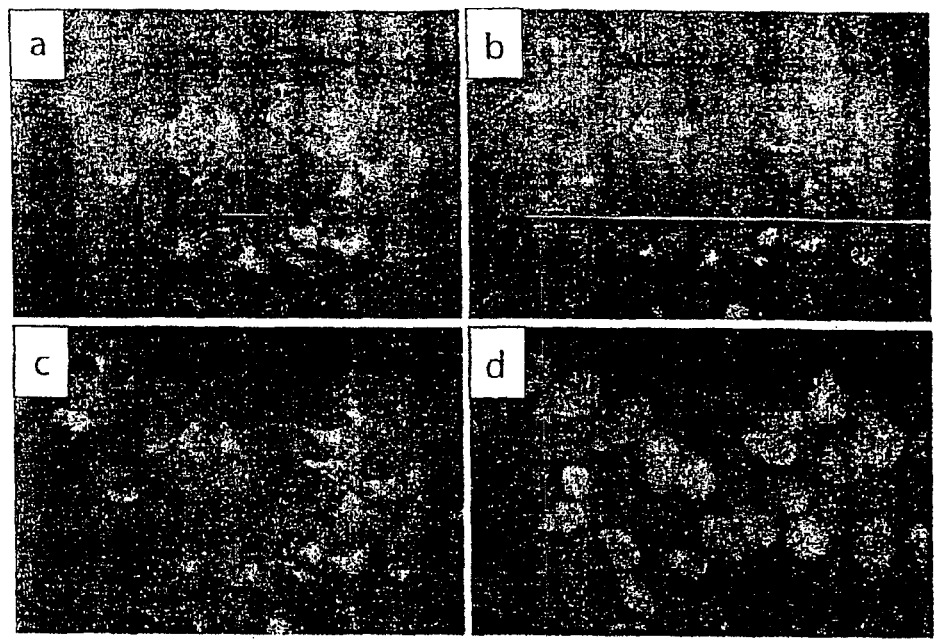
Figure 7
Figure 8
Western blotting
analysis of posterior
urethral secretion
(EECP targeting antibody)
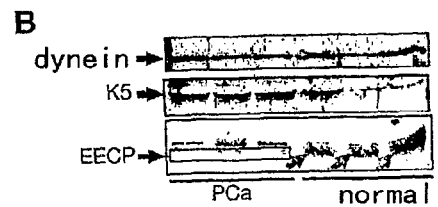
Western blotting analysis
of tissue lysates of
normal and malignant
prostate tissue
Figure 9

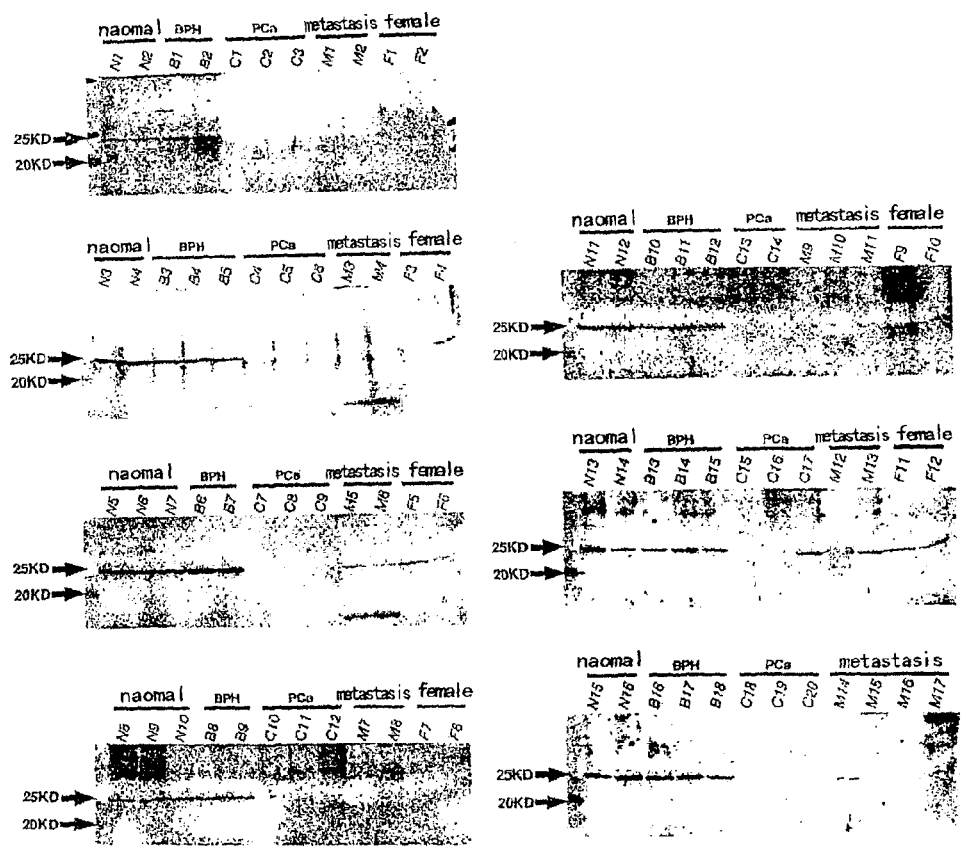

Figure 10

1. "N1"–"N16", Corresponding to 16 different male cases having no prostate injury by histodiagnosis
2. "B1"–"B18", Corresponding to 18 different male cases having benign hyperplasia of prostate by histodiagnosis
3. "C1"–"C20", Corresponding to 20 different male cases having prostate cancer by histodiagnosis
4. "M1"–"M17", Corresponding to 17 different male cases having prostate cancer and metastasis by histodiagnosis
5. "F1"–"F17", Corresponding to 12 different female cases having no clinical disease by histodiagnosis note: all the data of patients refer "Table 1"

Western blotting analysis on human plasma
(using EECP targeting antibody)

Western blotting analysis:
cellular lysate (transfected)
(transfected and endogenous)
(using EECP targeting antibody)

Western blotting analysis:
media supernatant of cultuerd cells
(transfected and endogenous)
human plasma
        (using EECP targeting antibody)

Western blotting analysis on
conditioned medium (0%FCS)
(using EECP targeting antibody)

SEQUENCE LISTING

<160> NUMBER OF SEQ ID NOS: 8

<210> SEQ ID NO 1
<211> LENGTH: 768
<212> TYPE: DNA
<213> ORGANISM: Homo sapiens

<400> SEQUENCE: 1

```
tcgcttcttc cttctggatg ggggcccagg gggcccagga gagtataaag gcgatgtgga      60
gggtgcccgg cacaaccaga cgcccagtca caggcgagag ccctgggatg caccggccag     120
aggccatgct gctgctgctc acgcttgccc tcctgggggg ccccacctgg cagggaaga     180 tgtatgccc tggaggaggc aagtatttca gcaccactga agactacgac catgaaatca     240
cagggctgcg ggtgtctgta ggtcttctcc tggtgaaaag tgtccaggtg aaacttggag     300
actcctggga cgtgaaactg ggagcctag gtgggaatac ccaggaagtc accctgcagc     360
caggcgaata catcacaaaa gtctttgtcg ccttccaagc tttcctccgg ggtatggtca     420
tgtacaccag caaggaccgc tatttctatt tgggaagct tgatggccag atctcctctg     480
cctaccccag ccaagagggg caggtgctgg tgggcatcta tggccagtat caactccttg     540
gcatcaagag cattggcttt gaatggaatt atccactaga ggagccgacc actgagccac     600
cagttaatct cacatactca gcaaactcac ccgtgggtcg ctagggtggg gtatggggcc     660
atccgagctg aggccatctg tgtggtggtg gctgatagta ctggagtaac tgagtcggga     720
cgctgaatct gaatccacca ataaataaag cttctgcaga atcagtgt                  768
```

<210> SEQ ID NO 2
<211> LENGTH: 90
<212> TYPE: DNA
<213> ORGANISM: Homo sapiens

<400> SEQUENCE: 2

```
atgggggccc aggggggccca ggagagtata aaggcgatgt ggagggtgcc cggcacaacc      60
agacgcccag tcacaggcga gagccctggg                                         90
```

<210> SEQ ID NO 3
<211> LENGTH: 208
<212> TYPE: PRT
<213> ORGANISM: Homo sapiens

<400> SEQUENCE: 3

```
Met Gly Ala Gln Gly Ala Gln Glu Ser Ile Lys Ala Met Trp Arg Val
1               5                   10                  15

Pro Gly Thr Thr Arg Arg Pro Val Thr Gly Glu Ser Pro Gly Met His
            20                  25                  30

Arg Pro Glu Ala Met Leu Leu Leu Thr Leu Ala Leu Leu Gly Gly
        35                  40                  45

Pro Thr Trp Ala Gly Lys Met Tyr Gly Pro Gly Gly Lys Tyr Phe
    50                  55                  60

Ser Thr Thr Glu Asp Tyr Asp His Glu Ile Thr Gly Leu Arg Val Ser
65                  70                  75                  80

Val Gly Leu Leu Leu Val Lys Ser Val Gln Val Lys Leu Gly Asp Ser
                85                  90                  95

Trp Asp Val Lys Leu Gly Ala Leu Gly Gly Asn Thr Gln Glu Val Thr
            100                 105                 110

Leu Gln Pro Gly Glu Tyr Ile Thr Lys Val Phe Val Ala Phe Gln Ala
        115                 120                 125

Phe Leu Arg Gly Met Val Met Tyr Thr Ser Lys Asp Arg Tyr Phe Tyr
    130                 135                 140

Phe Gly Lys Leu Asp Gly Gln Ile Ser Ser Ala Tyr Pro Ser Gln Glu
145                 150                 155                 160

Gly Gln Val Leu Val Gly Ile Tyr Gly Gln Tyr Gln Leu Leu Gly Ile
                165                 170                 175

Lys Ser Ile Gly Phe Glu Trp Asn Tyr Pro Leu Glu Glu Pro Thr Thr
```

```
                    180                 185                 190
Glu Pro Pro Val Asn Leu Thr Tyr Ser Ala Asn Ser Pro Val Gly Arg
                195                 200                 205

<210> SEQ ID NO 4
<211> LENGTH: 30
<212> TYPE: PRT
<213> ORGANISM: Homo sapiens

<400> SEQUENCE: 4

Met Gly Ala Gln Gly Ala Gln Glu Ser Ile Lys Ala Met Trp Arg Val
 1               5                  10                  15

Pro Gly Thr Thr Arg Arg Pro Val Thr Gly Glu Ser Pro Gly
            20                  25                  30

<210> SEQ ID NO 5
<211> LENGTH: 661
<212> TYPE: DNA
<213> ORGANISM: Homo sapiens
<220> FEATURE:
<221> NAME/KEY: CDS
<222> LOCATION: (1)..(534)
<223> OTHER INFORMATION:

<400> SEQUENCE: 5 atg cac cgg cca gag gcc atg ctg ctg ctg ctc acg ctt gcc ctc ctg      48
Met His Arg Pro Glu Ala Met Leu Leu Leu Leu Thr Leu Ala Leu Leu
 1               5                  10                  15 ggg ggc ccc acc tgg gca ggg aag atg tat ggc cct gga gga ggc aag      96
Gly Gly Pro Thr Trp Ala Gly Lys Met Tyr Gly Pro Gly Gly Gly Lys
            20                  25                  30 tat ttc agc acc act gaa gac tac gac cat gaa atc aca ggg ctg cgg     144
Tyr Phe Ser Thr Thr Glu Asp Tyr Asp His Glu Ile Thr Gly Leu Arg
        35                  40                  45 gtg tct gta ggt ctt ctc ctg gtg aaa agt gtc cag gtg aaa ctt gga     192
Val Ser Val Gly Leu Leu Leu Val Lys Ser Val Gln Val Lys Leu Gly
    50                  55                  60 gac tcc tgg gac gtg aaa ctg gga gcc tta ggt ggg aat acc cag gaa     240
Asp Ser Trp Asp Val Lys Leu Gly Ala Leu Gly Gly Asn Thr Gln Glu
65                  70                  75                  80 gtc acc ctg cag cca ggc gaa tac atc aca aaa gtc ttt gtc gcc ttc     288
Val Thr Leu Gln Pro Gly Glu Tyr Ile Thr Lys Val Phe Val Ala Phe
                85                  90                  95 caa gct ttc ctc cgg ggt atg gtc atg tac acc agc aag gac cgc tat     336
Gln Ala Phe Leu Arg Gly Met Val Met Tyr Thr Ser Lys Asp Arg Tyr
            100                 105                 110 ttc tat ttt ggg aag ctt gat ggc cag atc tcc tct gcc tac ccc agc     384
Phe Tyr Phe Gly Lys Leu Asp Gly Gln Ile Ser Ser Ala Tyr Pro Ser
        115                 120                 125 caa gag ggg cag gtg ctg gtg ggc atc tat ggc cag tat caa ctc ctt     432
Gln Glu Gly Gln Val Leu Val Gly Ile Tyr Gly Gln Tyr Gln Leu Leu
    130                 135                 140 ggc atc aag agc att ggc ttt gaa tgg aat tat cca cta gag gag ccg     480
Gly Ile Lys Ser Ile Gly Phe Glu Trp Asn Tyr Pro Leu Glu Glu Pro
145                 150                 155                 160 acc act gag cca cca gtt aat ctc aca tac tca gca aac tca ccc gtg     528
Thr Thr Glu Pro Pro Val Asn Leu Thr Tyr Ser Ala Asn Ser Pro Val
                165                 170                 175 ggt cgc tagggtgggg tatggggcca tccgagctga ggccatctgt gtggtggtgg      584
Gly Arg ctgatagtac tggagtaact gagtcgggac gctgaatctg aatccaccaa taaataaagc    644
```
ttctgcagaa tcagtgt                                                                661

<210> SEQ ID NO 6
<211> LENGTH: 178
<212> TYPE: PRT
<213> ORGANISM: Homo sapiens

<400> SEQUENCE: 6

Met His Arg Pro Glu Ala Met Leu Leu Leu Thr Leu Ala Leu Leu
1               5                   10                  15

Gly Gly Pro Thr Trp Ala Gly Lys Met Tyr Gly Pro Gly Gly Lys
            20                  25                  30

Tyr Phe Ser Thr Thr Glu Asp Tyr Asp His Glu Ile Thr Gly Leu Arg
        35                  40                  45

Val Ser Val Gly Leu Leu Leu Val Lys Ser Val Gln Val Lys Leu Gly
        50                  55                  60

Asp Ser Trp Asp Val Lys Leu Gly Ala Leu Gly Gly Asn Thr Gln Glu
65                  70                  75                  80

Val Thr Leu Gln Pro Gly Glu Tyr Ile Thr Lys Val Phe Val Ala Phe
                85                  90                  95

Gln Ala Phe Leu Arg Gly Met Val Met Tyr Thr Ser Lys Asp Arg Tyr
                100                 105                 110

Phe Tyr Phe Gly Lys Leu Asp Gly Gln Ile Ser Ser Ala Tyr Pro Ser
            115                 120                 125

Gln Glu Gly Gln Val Leu Val Gly Ile Tyr Gly Gln Tyr Gln Leu Leu
        130                 135                 140

Gly Ile Lys Ser Ile Gly Phe Glu Trp Asn Tyr Pro Leu Glu Pro
145                 150                 155                 160

Thr Thr Glu Pro Pro Val Asn Leu Thr Tyr Ser Ala Asn Ser Pro Val
                165                 170                 175

Gly Arg

<210> SEQ ID NO 7
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 7
cgcggtaccg gatccatgca ttggcggccg cgggaattc                                       39

<210> SEQ ID NO 8
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 8
cgcggtaccg gatccatgca tcatatggtc gacctgcag                                       39

POLYPEPTIDE, NUCLEIC ACID MOLECULE ENCODING IT AND THEIR USES

CROSS-REFERENCE TO RELATED APPLICATIONS

This application is the National Stage of International Application No. PCT/CN2007/002111, filed on Jul. 10, 2007, which claims the benefit of Chinese Application Serial No. 200610098727.3, filed on Jul. 10, 2006, the contents of both of the foregoing applications are hereby incorporated by reference in their entirety.

FIELD OF THE INVENTION

The present invention relates to a novel polypeptide, a nucleic acid molecule encoding the same, a recombinant vector and a host cell comprising the nucleic acid molecule, and the use of the polypeptide and nucleic acid.

BACKGROUND OF THE INVENTION

Human cells and other eukaryotes are subdivided by membranes into many functionally distinct compartments. Each membrane-bounded compartment, or organelle, contains different proteins essential for the function of the organelle. The cell uses "sorting signals" which are amino acid motifs located within proteins, to target proteins to particular cellular organelles.

One type of sorting signal, called signal sequence, signal peptide, or leader sequence, directs one type of proteins to an organelle called endoplasmic reticulum (ER). The ER separates the membrane-bounded proteins from all other types of proteins. Once localized to ER, both groups of proteins can be further directed to another organelle called Golgi apparatus. Here, the Golgi distributes the proteins to vesicles, including secretory vesicles, cell membranes, lysosomes, and other organelles.

Proteins targeted to the ER by a signal sequence can be released into the extracellular space as secreted proteins. For example, vesicles containing secreted proteins can fuse with the cell membranes and release their contents into the extracellular space—a process called exocytosis. Exocytosis can occur autonomously or after receipt of a triggering signal. In the latter case, the proteins are stored in secretory vesicles (or secretory granules) until exocytosis is triggered. Similarly, proteins residing on the cell membranes can also be secreted into the extracellular space by proteolytic cleavage of a "linker" which holds the proteins to the membrane.

Prostate cancer is the most frequently diagnosed cancer and second leading cause of cancer death in men. 45,000 men die annually of this disease. The chance for a man to develop invasive prostate cancer during his lifetime is 1 in 6. At the age of 50, a man has a greater than 40% chance of developing prostate cancer and nearly a 3% chance of dying from this disease. Although some advances in the treatment of locally confined tumors have been achieved, prostate cancer is incurable once it has metastasized. Patients with metastatic prostate cancer are treated with hormonal ablation therapy, but with only short-term success. Eventually, these patients develop an androgen-refractory state leading to disease progression and death.

A common and fundamental problem in the treatment of prostate cancer is the absence of reliable diagnostic and prognostic markers capable of accurately detecting early-stage localized tumors and/or predicting disease susceptibility and progression. Early detection and diagnosis of prostate cancer currently relies on prostate specific antigen (PSA) assays, digital rectal examination (DRE), transrectal ultrasonography (TRUS), and transrectal needle biopsy (TRNB). Serum PSA assays in combination with DRE represent the leading diagnostic approach at present. However, this diagnostic approach has severe limitations which have fueled intensive research into finding better diagnostic markers of this disease. A number of markers have been identified, but only PSA is in widespread clinical use. However, ideal prostate tumor markers have been extremely elusive and no marker has yet been proved reliable for predicting progression of the disease. Thus, there is a need for more reliable and informative diagnostic and prognostic methods in the treatment of prostate cancer.

In addition, there is also great interest in identifying prostate-specific proteins that could be appropriate as therapeutic targets, as there is no effective treatment for patients who develop recurrent disease or who have been diagnosed with metastatic prostate cancer. Although hormone ablation therapy can palliate these patients, the majority inevitably progress to develop incurable, androgen-independent prostate cancer (Lalani et al., 1997, *Cancer Metastasis Rev.* 16: 29-66).

PSA is a 33 kD glycoprotein synthesized in the epithelial cells of the prostate gland. It is a secreted serine protease of the kallikrein family. The mature form of PSA takes isoleucine as the N-terminal and has 237 amino acid residues with a molecular mass of 28,400 D.

PSA is the most widely used tumor marker for screening, diagnosing, and monitoring prostate cancer today. In particular, serum PSA immunoassays are in widespread clinical use. Recently, a reverse transcriptase-polymerase chain reaction (RT-PCR) assay for PSA mRNA in serum has been developed. However, PSA is not a prostate cancer-specific marker, since elevated levels of PSA are detectable in a large percentage of patients with BPH and prostatitis (25-86%) (Gao et al., 1997, *Prostate* 31: 264-281), as well as in other nonmalignant diseases and in some normal men, which is a factor significantly limits the diagnostic specificity of this marker. For example, elevations in serum PSA of between 4 to 10 ng/ml are observed in BPH, and even higher values are observed in prostatitis, particularly in acute prostatitis. BPH is an extremely common condition in men. Further confusing the situation is the fact that serum PSA elevation is observed without any indication of disease from DRE, and vice-versa. Moreover, it is now recognized that PSA not only presents in the prostate but also has a variety of complex biological activities (See e.g. Fortier et al., *J. Natl. Cancer Inst.* 1999, 91(19):1635-40).

While PSA-based assays are useful in the diagnosis of prostate disease, they are not sufficiently specific to distinguish the benign prostate hyperplasia (BPH) from prostate cancer (PCa). Several different approaches have been taken to improve the specificity of PSA-based assays. For example, recently, it has been found that the elevated levels of PSA (free PSA) inactive and non-complexed with alpha1-antichymotrypsin (ACT) in the serum of men with prostate cancer have been correlated with benign prostatic disease. However, none of these methodologies have been able to reproducibly distinguish benign from malignant prostate disease. In addition, PSA diagnostics has sensitivity of 57-79% (Cupp & Osterling, 1993, *Mayo Clin Proc* 68:297-306), and thus a significant population of men with the prostate cancer will be missed diagnosis.

Prostate-Specific Membrane Antigen (PSMA) is a recently described cell surface marker of prostate cancer which has been evaluated in various studies for its usage as a diagnostic and therapeutic marker. PSMA expression is largely restricted to prostate tissues, but detectable levels of PSMA mRNA have been observed in brain, salivary gland, small intestine, and renal cell carcinoma (Israeli et al., 1993, *Cancer Res* 53: 227-230). PSMA protein is highly expressed in most primary and metastatic prostate cancers, but is also expressed in most intraepithelial neoplasia specimens (Gao et al., supra). Preliminary results using an Indium-111 labeled, anti-PSMA monoclonal antibody to image recurrent prostate cancer show some promise (Sodee et al., 1996, *Clin Nuc Med* 21: 759-766). PSMA is a hormone dependent antigen requiring the functional androgen receptor. Since not all the prostate cancer cells express androgen receptor, the clinical utility of PSMA as a therapeutic target is inherently limited. Clinical trials designed to examine the effectiveness of PSMA immunotherapy are also underway.

Prostate Stem Cell Antigen (VISTA) is another recently described cell surface marker of prostate cancer (Reiter et al., 1998, *Proc. Natl. Acad. Sci. USA* 95: 1735-1740). PSCA expression has been shown to be predominantly prostate specific and widely highly expressed across all stages of prostate cancer, including high differentiated prostatic intraepithelial neoplasia (PIN), androgen-dependent and androgen-independent prostate tumors. The PSCA gene has been mapped to chromosome 8q24.2, more than 80% of prostate cancers have a region of allelic. PSCA shows promise as a diagnostic and therapeutic target in view of its cell surface localization, prostate specificity, and upregulated expression in prostate cancer cells.

Progress in the identification of specific markers is slow due to lack of experimental animal model systems that recapitulate clinical prostate cancer. Attempted solutions to this problem have included the generation of prostate cancer cell lines (Horoszewicz et al., 1983, *Cancer Res.* 43, 1809) and prostate cancer xenografts (Pretlow et al., 1991, *Cancer Res.* 51, 3814; van Weerden et al., 1996, *Am. J. Pathol.* 149, 1055; Klein et al., 1997, *Nature Med.* 3, 402). However, these approaches only gain limited success. For example, xenografts have generally produced low long-term survival rates. In addition, none of the most widely used human prostate cancer cell lines—PC-3, DU-145, and LNCaP—can reproducibly give rise to osteoblastic lesions typical of prostate cancer. A further limitation of the DU-145 and PC-3 cell lines is that these cells do not express prostate specific antigen (PSA) or androgen receptor (AR) (Kaighn et al., 1979, *Invest. Urol.* 17: 16-23; Gleave et al., 1992, *Cancer Res.* 52: 1598-1605), questioning their relevance to clinical prostate cancer. The LNCaP cell line is androgen responsive and expresses PSA, but contains a mutation in the androgen receptor which alters the ligand specificity.

Recently, a series of prostate cancer xenografts (derived from patient tumors) demonstrating genetic and phenotypic characteristics similar to the human clinical situation have been described (Klein et al., 1997, *Nature Med.* 3: 402). These LAPC (Los Angeles Prostate Cancer) xenografts have survived more than one year in severe combined immune deficient (SCID) mice. The LAPC-4 xenograft model system has the capacity to mimic the transition from androgen dependence to androgen independence and the progress of metastatic lesions (Klein et al., 1997, supra). LAPC-4 tumors regress in male mice after castration, but re-grow within 2-3 months as androgen independent tumors. Both androgen dependent (AD) and androgen independent (AI) LAPC-4 xenograft tumors express equal levels of the prostate specific markers PSA, PSMA and PSCA (prostate stem cell antigen), which are identified using representational difference analysis of cDNAs derived from the AD and AI variants of the LAPC-4 xenograft tumors.

In one of the earliest studies on free PSA isolated from seminal plasma, internal cleavage sites at Arg85, Lys145, and Lys182 (mistakenly identified as Lys185) were observed (Watt, K. W. K., et al., *Proc Natl Acad Sci USA*, 83: 3166-3170, 1986). Subsequent studies have focused largely on the predominant cleavage site at Lys145 (present in 30-40% of the PSA). The presence of Lys145 cleavage is correlated with the inactivation of PSA and attributed to a random physiological cleavage, which occurs sometimes after PSA expression. The minor levels of cleavages at Arg85 and Lys182 largely ignored have also been observed (Zhang, W. M., et al., *Clin Chem*, 41: 1567-1573, 1995).

PSA has already been isolated from BPH tissue nodules in order to determine whether this form of PSA is different from seminal plasma PSA. BPH nodules comprise a mixture of stromal components and tightly packed epithelial ductal cells, and are visible by either macroscopic examination or low power microscopy of stained prostate tissue sections. The development of BPH nodules is highly correlated with increased prostate volume. The biochemical changes associated with nodular development may therefore play a role in the overall enlargement of the prostate, and in the clinical symptoms associated with BPH. PSA from BPH nodules has been found to contain a higher percentage of internal cleavages at Ile1, His54, Phe57, and Lys146 than seminal plasma PSA. These cleavages are thought to account for the lower enzymatic activity of PSA from BPH nodules as compared to that of the seminal plasma PSA (Price, H., et al., *Hum Pathol*, 21: 578-585, 1990.).

SUMMARY OF THE INVENTION

In one aspect, the present invention relates to a polypeptide, which contains the antigenic epitope of the amino acid sequence of SEQ ID NO: 3, the preferable polypeptide comprises the amino acid sequence selected from: the amino acid sequence of SEQ ID NO: 3; the amino acid sequence of SEQ ID NO:3 at position 16 to 32, position 1 to 30, position 50 to 80, position 170 to 200 of the amino acid.

In another aspect, the present invention relates to an isolated polynucleotide, which has the coding sequence of the above polypeptide. The preferable polynucleotide comprises the polynucleotide sequences selected from: polynucleotide sequence of SEQ ID:1; the polynucleotide sequence of SEQ ID NO:1 at position 2 to 768, 18 to 644, 1 to 107, 54 to 107, 18 to 54 of the polynucleotide. The preferable nucleic acid is DNA.

In still another aspect, the present invention relates to a recombinant vector, which contains the above polynucleotide. Preferably, the polynucleotide is operably ligated to a promoter.

In yet another aspect, the present invention relates to a recombinant host cell.

The present invention further relates to a use of the above polypeptide or polynucleotide for preparing an reagent, a kit or a device for diagnosing the diseases characterized in the expression of EECP. The diseases are selected from: prostate cancer, breast cancer, stomach cancer, and colon cancer. The diagnostic agent for the diseases characterized in the expression of EECP is the aforesaid monoclonal antibody or polyclonal antibody.

The present invention further relates to a use of a substance increasing or inhibiting the expression and/or activity of EECP for preparing a drug for treating or preventing the diseases characterized in the expression of EECP. Such diseases characterized in the expression of EECP are selected from: prostate cancer, breast cancer, stomach cancer and colon cancer. The substance increasing or inhibiting the expression and/or activity of EECP is selected from sense EECP cDNA, full length or partial EECP, proteinases which degrade EECP specifically, antibody specifically bind to EECP, anti-sense cDNA which inhibits the expression of EECP, ribozyme which inhibits the expression of EECP or siRNA that specifically inhibits the expression of EECP directly. In a preferable embodiment, the substance increasing or inhibiting the expression and/or activity of EECP is used in combination with radio therapy, chemotherapy, hormone or bio-cancer drugs.

The present invention relates to methods and compositions for the diagnosis and treatment of prostate and breast cancer, derived from or based on a novel gene EECP and extensively described herein. A full length cDNA comprising the entire coding sequence of the EECP gene is provided (FIG. 1). This cDNA encodes a protein which is highly related to, but structurally distinct from, the recently published HRPE773 (Hilary F. Clark et al., 2003, *Genome Research* 13: 2265-2270). The EECP gene also shows a very different expression pattern relative to the expression profile of HRPE773.

In another aspect, the present invention provides a EECP polypeptide, which can be a full-length EECP protein or a fragment thereof or an analog or homolog thereof.

More specifically, the present invention provides polynucleotides corresponding to all or part of the EECP gene and the complementary sequence thereof, as well as mRNA, and coding sequence, including polynucleotides encoding EECP protein and fragments thereof, DNA, RNA, DNA/RNA hybrid, and related molecules, polynucleotides or oligonucleotides complementary to the EECP gene or mRNA sequence or parts thereof, and polynucleotides or oligonucleotides which hybridize to the EECP gene, mRNA, or EECP-encoding polynucleotides. Also provided is a method for isolating cDNA and EECP-encoding gene. Recombinant DNA molecules containing EECP polynucleotides, cells transformed or transduced with such molecules, and host-vector systems for the expression of EECP gene products are also provided. The present invention further provides an EECP protein and polypeptide fragments thereof.

The present invention provides a method for detecting the presence of EECP polynucleotide and protein in various biological samples, as well as a method for identifying cells that express EECP. The present invention further provides a prognostic and diagnostic method for examining a biological sample to show the cancer occurrence in a given patient by comparing the status of EECP in the biological sample to the status of EECP in a corresponding normal sample, wherein alterations in the status of EECP in the biological sample are associated with cancer occurrence in said given patient. The present invention further provides various diagnostic compositions and strategies for diagnosing prostate cancer and breast cancer.

The present invention further provides various therapeutic compositions and strategies for treating prostate cancer and breast cancer, particularly including: EECP polypeptide and EECP antibody treatment methods and compositions, cancer vaccines, and small molecule therapy.

The present invention provides antibodies that bind to EECP protein and polypeptide fragments thereof, including polyclonal and monoclonal antibodies, murine and other mammalian antibodies, chimeric antibodies, humanized and fully human antibodies, and antibodies labeled with a detectable marker or toxin or therapeutic composition. These and other EECP antibodies are useful in molecular diagnostic assays and diagnostic imaging methods for detecting, localizing and characterizing cancer of the prostate and breast and metastases thereof.

The Sequence Listing submitted electronically as an ASCII text file is incorporated by reference. This text file, named as 67228.txt, was created on Jan. 8, 2009 and has a size of 9 kilobytes.

BRIEF DESCRIPTION OF THE FIGURES

FIG. 1. Nucleotide sequence of full length cDNA (SEQ ID NO: 1) of EECP and a portion thereof (SEQ ID NO: 2). The nucleotides contain the coding region of the EECP gene which encodes EECP protein (full length or a portion).

FIG. 2. The amino acid sequence (SEQ ID NO: 3) of EECP protein deduced from its cDNA sequence (SEQ ID NO: 1). The amino acid sequence (SEQ ID NO: 4) of a portion of the EECP protein deduced from its cDNA sequence (SEQ ID NO: 2).

FIGS. 3A-B. FIG. 3A shows the nucleotide and amino acid sequence of EECP cDNA and protein. FIG. 3B shows a schematic representation of the reading frame of EECP.

FIG. 4. The cDNA sequence of HRPE773 (SEQ ID NO: 5) and the protein sequence (SEQ ID NO: 6) encoded thereby. The recently published HRPE773 (Hilary F. Clark et al., 2003, *Genome Research* 13: 2265-2270) is a protein which is related to, but structurally distinct from, the EECP protein.

FIG. 5. The translation product of this gene shares sequence homology with previously published sequences. An amino acid sequence alignment comparing EECP with the previously published sequence of HRPE773 (Hilary F. Clark et al., 2003, *Genome Research* 13: 2265-2270), and the published sequence of "similar to common salivary protein 1" (LOC124220) (Strausberg R. L., et al., 2002, *Proc. Natl. Acad. Sci. U.S.A.* 99 (26), 16899-16903). The differences in the numbers of amino acid are shown in green (between HRPE773 and "similar to common salivary protein 1") and red (between EECP and HRPE773) bar. The differences in the numbers of amino acid constructing the three proteins are also indicated. The sizes of the predicted molecular weights of the three proteins are also marked. All of the three genes are thought to reside on chromosome 16.

FIG. 6. Characterization of Monoclonal antibodies directed against EECP. Monoclonal antibodies towards EECP are generated using a purified GST-EECP fusion protein. Monoclonal antibodies are screened by Western blotting against cellular lysates derived from Du145 cells transfected with a pSG5 vector with the insertion which encoding EECP-Flag, media supernatant of these transfected cultured cells and human plasma. (A) antibody (10F6) that specifically recognizes the amino acids of EECP at position 56 to 70 are used for Western blotting, Lane 1: lysates of pSG5-Flag transfected cell (as control); Lane 2: lysates of pSG5/EECP-Flag transfected cell; Lane 3: supernatant of pSG5-Flag transfected cell (as control); Lane 4: supernatant of pSG5/EECP-Flag transfected cell; Lane 5: plasma of the patients suffering from tumor; Lane 6: plasma of normal human. (B) antibody (5D5) that specifically recognizes the amino acids of EECP at position 19 to 32 are used for Western blotting, Lane 1: supernatant of pSG5-Flag transfected cell (as control); Lane 2: supernatant of pSG5/EECP-Flag transfected cell; Lane 3-4: endogenous secretion in the supernatant of the cultured cells: the cultured cells supernatant collected after culturing the untransfected LNCap for 6 hours and 24 hours to 80% confluence. Molecular weight standards are indicated on one side in kilodaltons (KD).

FIG. 7. Immunocytochemistry of EECP. 22RV1 cell line is in normal culture condition (10% FCS, no additional androgen or other related products). (a) EECP is recognized by 10F6 as primary antibody, and Cy3 conjugated goat-anti-mouse as secondary antibody. (b) The Golgi body is recognized by FITC conjugated wheat germ agglutinin. (c) Merged photo shows the co-localization of EECP and Golgi body. (d) DAPI stain presents the cellular nucleus.

FIG. 8. Immunohistochemical analysis of normal and malignant prostate samples with anti-EECP monoclonal antibody (MAb). Samples include: (Normal) normal prostate tissue stained with 10F6; (PCa) prostate cancer tissue stained with 10F6. All pictures are at 400 times magnification. For example, the staining localization of EECP in normal prostate and prostate cancer show distinct differences in the accumulation of EECP: EECP expresses mainly in the basal layer cells of normal acini of prostate; but the protein heterogenously expresses in the malignant prostate tissue. Moreover, the EECP expression level is lower in the malignant cells as compared to the normal basal layer cells. This finding also provides confirmatory evidence for the use of EECP as a diagnostic and therapeutic target of prostate cancer.

FIG. 9. Western Blotting assays on the prostate tissue lysates and posterior urethral secretion. (A) De-glycosylation of EECP in posterior urethral secretion. EECP in posterior urethral secretion (from a normal male donor) is purified using Nickel-agarose. EECP protein is then de-glycosylated using N-glycosidase F. Untreated EECP (lane 1) and de-glycosylated protein (lane 2) are analyzed by Western blotting using anti-EECP antibody 10F6. Molecular weight standards are indicated on one side in kilodaltons (KD). (B) Tissue lysates of malignant and normal part of prostate tissue, from six different cases of patients received prostatectomy. Both of "normal" and "PCa" part of tissue are first histologically diagnosed by frozen section on the frozen tissue mass, and then micro-dissected in the frozen form. The micro-dissection process (from the first to the last cutting) is checked by microscopic analysis by histologist. The lysates are analyzed by 10% and 12% SDS-PAGE, and probed to antibodies against: "Dynein", for loading control; "K5", for quantity control of karatinocytes; and 10F6 for EECP. EECP expression in "normal" tissue is marked by arrows in green color. The expression lost in tumor tissue is indicated in the red square.

FIG. 10. Western Blotting analysis of human plasma. Human plasma samples are treated by albumin depletion kits from SIGMA and VIVAscience, according to the instruction of manufactory. The albumin depleted plasma is analyzed by 12% SDS-PAGE. 1 μl plasma from each patient is loaded. Normalization of loading is verified by Ponceau S staining of nitrocellulose membranes following transfer. And the membrane is probed to antibodies against EECP (10F6). Arrows indicate the 25 kD full length EECP protein. The results show a lack of expression of EECP in 95% of the samples from prostate cancer patients, which provides confirmatory evidence for the use of EECP as a diagnostic and therapeutic target of prostate cancer. Moreover, the partial expression of the protein in some prostate cancer metastasis cases normally receiving un-invasive treatment only, indicating that the EECP can be used as a prognostic marker and a marker of treatment effect. Additional important point is that the expression level of EECP in female is only a fraction of the level of normal male, which strongly suggests that the EECP level in circulation is mainly related to the endo-secretion of EECP of the male genital organs.

medium supernatant of cultured cells is from those Du145 cells transfected with either EECP (lane "EECP") or pSG5-Flag (as a control, lane "vector"). For endogenous EECP analysis, another prostate cancer cell line (LNCap) is chosen to grow in 2% FCS medium. The endogenous secretion of EECP in the medium supernatant of cultured cells is analyzed in the same gel. The medium is collected after culturing the cells for 6 hours and 24 hours to 80% confluence. Molecular weight standard is indicated on one side in kilodaltons (KD). It is worth notice that, the same as 22RV1, in the secretion of LNCap cell line, there is also the same shorter form of the protein detected by the antibody, of which size is clearly lower than the full length EECP and about 22 KD. More importantly, the EECP expressed in human plasma (without treatment of albumin depletion) is detected to have the same size of 25 KD as in vitro secreted form of EECP, either transfected or endogenous.

Figure 15:
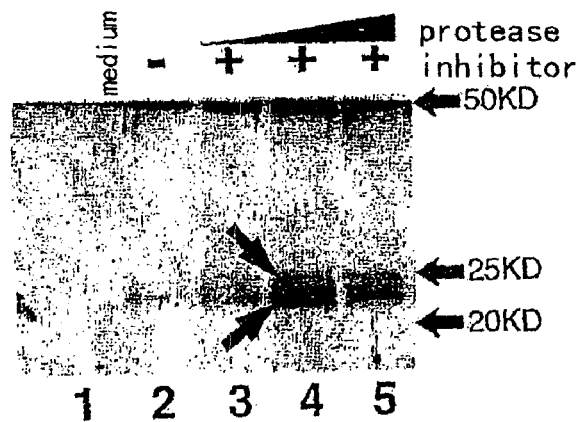

FIG. 15. Western blotting analysis of in vitro secreted endogenous EECP (in 0% FCS): EECP is proteolytically cleaved or degraded by proteases. 22RV1 cell line is cultured in serum-free culture condition (0% FCS, no additional androgen or other related products) at 80% confluence. In such condition, the proteases sensitive proteins lack the non-specific protection from serum. (Lane 1) medium (0% FCS) used for 22RV1 cell culture. (Lane 2) conditioned medium of 22RV1 culturing. (Lane 3 to 5) conditioned medium of 22RV1 culturing, adding different dosage of protease inhibitor. This result provides confirmatory evidence of that the protein EECP is proteolytically cleaved or degraded by proteases.

DETAILED DESCRIPTION OF THE INVENTION

Unless otherwise defined, all the terms of art, notations and other scientific terminology used herein are intended to have the meanings known or commonly employed by those of skill in the art to which this invention pertains. The techniques and procedures described or referenced herein are generally well understood and commonly employed using conventional methodology by those skilled in the art, such as, for example, the widely utilized molecular cloning methodologies described in Sambrook et al., 1989, *Molecular Cloning: A Laboratory Manual*, 2d ed., Cold Spring Harbor Laboratory Press, Cold Spring Harbor, N.Y. As appropriate, procedures involving the use of commercially available kits and reagents are generally carried out in accordance with the manufacturer defined protocols and/or parameters unless otherwise indicated.

As used herein, the term "polynucleotide" means a polymeric form of nucleotides of at least 10 bases or base pairs in length, either ribonucleotide or deoxynucleotide or a modified form of either type of nucleotide, and is meant to include single and double stranded forms of DNA.

As used herein, the term "polypeptide" means a polymer of at least 6 amino acids. Throughout the specification, standard three letter or single letter designation for amino acids are used. In this context, "EECP polypeptide" includes, for example, a protein having the 208 amino acids sequence shown in FIG. 2 (SEQ ID NO 3) and FIG. 3 as well as the domain of about 30 amino acids shown in FIG. 2 (SEQ ID NO 4).

In the context of amino acid sequence comparison, the term "identity" is used to express the percentage of amino acid residues at the same relative positions are the same. Also in this context, the term "homology" is used to express the percentage of amino acid residues at the same relative positions are either identical or similar, using the conserved amino acid criteria of BLAST analysis, as is generally understood in the art. For example, % identity values may be generated by WU-BLAST-2 (Altschul et al., 1996, Methods in Enzymology 266:460-480; blast.wustl/edu/blast/README.html). Further details regarding amino acid substitutions which are considered conservative under such criteria are provided below.

Additional definitions are provided throughout the subsections that follow.

The present invention relates to methods and compositions for the diagnosis and treatment of certain cancers using isolated polynucleotide corresponding to the EECP gene, protein encoded by the EECP gene and fragments thereof, and antibodies capable of specifically recognizing and binding to EECP protein. Throughout the Application, the methods and compositions are representatively described for the diagnosis and treatment of prostate and breast cancers.

The nucleotide and deduced amino acid sequences of the novel EECP gene are shown in FIGS. 1 and 2. The EECP gene encodes a predicted 208 amino acids protein, containing multiple domains including a domain (from its $31^{st}$ amino acid to the $208^{th}$ amino acid) that has been described as HRPE773 (Hilary F. Clark et al., 2003, *Genome Research* 13: 2265-2270), as shown in FIG. 4 and FIG. 5. At the same time, the EECP gene encoding 208 amino acids also contains a domain (from its $37^{th}$ amino acid to the $208^{th}$ amino acid) that has been described as "similar to common salivary protein 1" (Strausberg R. L. et al., 2002, *Proc. Natl. Acad. Sci. U.S.A.* 99 (26), 16899-16903), as shown in FIG. 5. Both of the HRPE773 and "similar to common salivary protein 1" have been mapped to chromosome 16, the same chromosome as EECP located.

The applicant have cloned a full length cDNA comprising the entire coding region of the EECP gene, but it contains an extra 90-polynucleotides domain sequence compared to the published sequence of HRPE773. This 90-polynucleotides sequence does not exist in the cDNA sequence of HRPE773. The specific nature and significance of this difference is presented in FIGS. 5, 8, 9, 10, 11, 13 and 14. Consequently, a protein having the sequence described by Hilary F. Clark et al. may have a significantly different functional activity from the protein described herein. Moreover, it is known in the art that such gene possesses a certain amount of variability and that this variability can effect various aspects of cell physiology, including those associated with oncogenesis (see e.g. Rebbeck et al., *J. Natl. Cancer Inst.* 90(16): 1225-1229 (1998) and Tonin et al., *Semin. Surg. Oncol.* 18(4): 281-286 (2000)). In addition, the novel EECP newly discovered by the applicant has a completely different expression pattern in comparison to what has been known for the previously reported HRPE773 and "similar to common salivary protein 1".

EECP is predominantly expressed in the basel layer cells of normal prostate acini. The expression level decreases dramatically and the expression level is hetrogenous in the malignant acini. In breast, EECP expresses not only in normal secretion and ductal cells, but also in malignant cells at the same or even higher level.

The prostate gland and its secretions have long been known to contain a variety of potent proteolytic activities (Mann and Lutwak-Mann, 1981). The proteases secreted into the semen have been postulated to degrade seminal proteins, especially to produce liquefaction of seminal coagulum in humans, and to possibly interact with sperm so as to modify their cell surfaces and affect their fertilizing ability. In human prostate tumors, it is demonstrated that they have substantially increased level of different type of proteases, such as Cathepsin B, type IV collagenase, matrilysin, matrix metalloproteases collagenase and stromelysin. Moreover, due to the damage of the patent basement membrane that normally separate the secretion and epithelial cell sources of proteases from stoma, massive amount of different types of proteases are released into the circulation in prostate cancer patients, such as the case of PSA (reviewed by Michael J. Wilson, *Microscopy Res. And Technique*, 1995, 30:305-318). Since the inventor has shown that EECP is highly expressed in basal epithelial cells and to a lesser extent in secretory cells in normal human prostate, and is detected also in the posterior urethral secretion. It is reasonable to predict that EECP can be degraded by the prostate secreted proteases. And this prediction is proved in vitro also by the inventor, as shown in FIG. 15.

Part of the EECP sequence is isolated during the comparison course of a transcriptome-level, by differential display, of a series of macro-dissected tumor biopsies of prostate cancer. The differential band is isolated and cloned into the pGEMt-easy vector where the clone containing the fragment that has generated the original differential display profile is identified by Reverse Northern hybridization (not shown). Sequence analysis of the clone with the BLAST search algorithm (www.ncbi.nlm.nih.gov/blast) indicates that it consists of a 500 bp fragment corresponding to a sequence on the *H. sapiens* Chromosome 16, cosmid clone 352F10 (LANL) (AC005361). To begin the analysis of this novel gene, the full-length cDNA is amplified and cloned by 5'/3' RACE PCR from a normal prostate library (Clontech). The full-length cDNA is made up of four exons and localizes to Chromosome 16p12.3 (FIG. 3).

Figure 11:
FIG. 11. Immunohistochemical analysis of normal and malignant breast samples with anti-EECP MAb. Samples include: (Normal) normal breast tissue stained with 10F6; (Tumor) matched adjacent tissues of breast cancer stained with 10F6. All pictures are at 400 times magnification. For example, the staining localization of EECP in normal breast and breast cancer show distinct differences in the accumulation of EECP: EECP expresses exclusively in the secretion cells of normal gland of breast and ductal cells. The secretion of EECP into the duct is clearly shown. But What is different from prostate cancer is that the protein is highly expressed in the malignant breast tissue, which normally lost the regular tissue structure, indicating that massive amount of EECP are released into the circulation system through the damaged basement membrane in breast cancer tissue. This finding also provides confirmatory evidence for using EECP as a diagnostic and therapeutic target of breast cancer.
Figure 12:
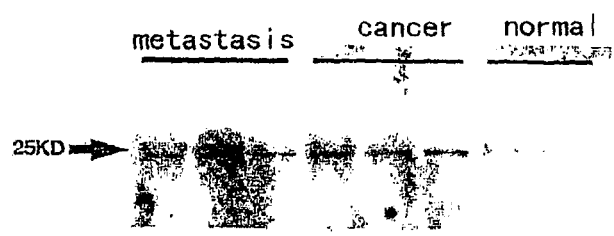
FIG. 12. Western Blotting analysis of human plasma. Human plasma samples are treated by albumin depletion kits from SIGMA and VIVAscience, according to the instruction of manufactory. The albumin depleted plasma is analyzed by 12% SDS-PAGE. 1 μl plasma from each patient is loaded. Normalization of loading is verified by Ponceau S staining of nitrocellulose membranes following transfer. And the membrane is probed to antibodies against EECP (10F6). Arrows indicate the 25 kD full length EECP protein. Increased level of expression of EECP in the samples from breast cancer and metastasis patients provides confirmatory evidence for using EECP as a diagnostic and therapeutic target of breast cancer. Importantly, the expression-difference-pattern between breast "normal" and "cancer" is different from those in prostate. In fact, it is just in contrary. In breast cancer cases, the circulation level of EECP is higher than in normal cases.
Figure 13:
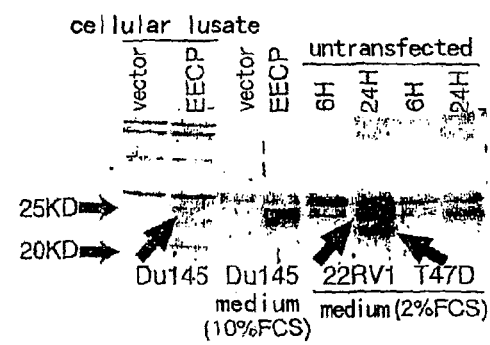
FIG. 13. Western Blotting analysis of transfected and endogenous EECP expression: the EECP protein is expressed as a full length and proteolytically cleaved form in cell lines. For the transfected EECP assays, Du145 cells are transfected with a pSG5 vector with the insertion which encoding EECP-Flag, both of the cell lysates and the media supernatant of these transfected cultured cells are collected for 12% SDS-PAGE gel and probed to 10F6 antibody. The collected cell lysates includes Du145 cells transfected with either EECP (lane "EECP") or pSG5-Flag (as a control, lane "vector"). (medium 10% FCS) medium supernatant of cultured cells is from those Du145 cells transfected with either EECP (lane "EECP") or pSG5-Flag (as a control, lane "vector"). Since the same proportion of "cell lysis" and "medium" samples are loaded, it is clear that major portions of EECP generated by cells are secreted into their growing environment. For endogenous EECP analysis, the prostate cancer (22RV1) and breast cancer (T47D) cell lines are chosen to grow in 2% FCS medium. The endogenous secretions of EECP in the medium supernatant of cultured cells are analyzed in the same gel. The medium supernatant is collected after culturing the cell for 6 hours and 24 hours to 80% confluence. Molecular weight standards are indicated on one side in kilodaltons (KD). It is worth notice that, in the secretion of 22RV1 cell line, there is a shorter form of the protein detected by the antibody, of which size is clearly lower than the full length EECP and about 22 KD. It is possibly a splicing variant of the full length EECP, or a proteolytically cleaved form of full length protein of EECP.
Figure 14:
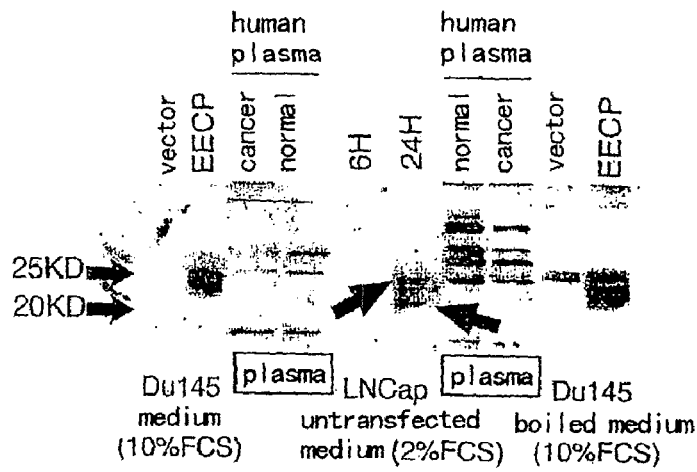
FIG. 14. Western Blotting analysis of transfected and endogenous EECP expression, and EECP expression in human plasma. For the transfected EECP assays, Du145 cells are transfected with a pSG5 vector with the insertion which encoding EECP-Flag, only medium supernatant of these transfected cultured cells are collected for 12% SDS-PAGE gel and probeed to 10F6 antibody. (medium 10% FCS)

Expression analysis shows the full length EECP presents a high level expression in plasma of all "normal" and "benign prostate hyperplasia" patients tested, but this expression is lost in those of over 95% of "prostate cancer" and "metastasis" cases (FIG. 10). Approximately, the same pattern is seen in prostate lysates (FIG. 9B). In addition, lower level expression of EECP is detected by immunohistochemical analysis in a number of prostate cancer samples (FIG. 8). More importantly, the expression level of EECP is dramatically lower in normal female compared to normal male (FIG. 10). This strongly suggests that the endo-secretion of male genital organ is the major source of the EECP level in circulation. Furthermore, Table 1 shows that the PSA level and the ratio between different types of PSA have no significant differences between the group of "BPH" and "PCa". These results indicate that the EECP gene is a predominantly prostate specific gene which may be involved in the development and/or progression of prostate cancer. Moreover, higher level expression of EECP is detected by Western blot in plasma of a number of breast cancer and metastasis patients, when comparing to "normal" (FIG. 12); high level expression of EECP is detected by immunohistochemical analysis in a number of breast cancer samples (FIG. 11). These data presented herein indicate that EECP is a secreted molecule, the level in the circulation is highly related to malignant changes in prostate and breast. Consequently, Such data provides evidence that the expression level of EECP in circulation of patient bearing prostate or breast cancers can provide a molecular basis for detecting, diagnosing, prognosing and/or treating these cancers in the said patients, since the EECP expression is lost or decreased significantly in the plasma (serum) of the prostate cancer patients while in the plasma (serum) of the breast cancer patients, EECP improves greatly.

TABLE 1

Relevant data of the PSA expression in the serum sample of the patients shown and detected in FIG. 10.

| Group | age | gender | free PSA (%) | PSA | cPSA | serum | tumor tages | Gleason score |
|---|---|---|---|---|---|---|---|---|
| n1 | 42 | M | | 0.55 | 0.3 | normal | | |
| n2 | 43 | M | | 0.6 | 0.39 | normal | | |
| n3 | 41 | M | | 1.15 | 0.96 | normal | | |
| n4 | 51 | M | 23.9 | 1.55 | 1.35 | normal | | |
| n5 | 41 | M | | 0.45 | 0.35 | normal | | |
| n6 | 42 | M | | 1.13 | 0.96 | normal | | |
| n7 | 54 | M | | 0.82 | 0.73 | normal | | |
| n8 | 47 | M | | 0.5 | 0.29 | normal | | |
| n9 | 47 | M | | 0.67 | 0.34 | normal | | |
| n10 | 47 | M | | 0.24 | 0.13 | normal | | |
| n11 | 50 | M | | 0.86 | 0.81 | normal | | |
| n12 | 49 | M | | 0.65 | 0.53 | normal | | |
| n13 | 51 | M | | 0.32 | 0.2 | normal | | |
| n14 | 45 | M | | 0.92 | 0.72 | normal | | |
| n15 | 41 | M | | 0.72 | 0.71 | normal | | |
| n16 | 61 | M | | 0.41 | 0.21 | normal | | |
| b1 | 51 | M | 12 | 3 | 2.84 | benign prostate hyperplasia patient | | |
| b2 | 57 | M | 12.2 | 2.7 | 3.21 | benign prostate hyperplasia patient | | |
| b3 | 49 | M | 10.1 | 4.52 | 3.17 | benign prostate hyperplasia patient | | |
| b4 | 62 | M | 17.4 | 7.94 | 6.76 | benign prostate hyperplasia patient | | |
| b5 | 49 | M | 10.2 | 4.63 | 4.35 | benign prostate hyperplasia patient | | |
| b6 | 57 | M | | 2.81 | 2.53 | benign prostate hyperplasia patient | | |
| b7 | 66 | M | 14.9 | 3.36 | 2.13 | benign prostate hyperplasia patient | | |
| b8 | 49 | M | 16.4 | 5.74 | 4.26 | benign prostate hyperplasia patient | | |
| b9 | 64 | M | 14.1 | 8.44 | 5.92 | benign prostate hyperplasia patient | | |
| b10 | 68 | M | 13.2 | 5.62 | 4.43 | benign prostate hyperplasia patient | | |
| b11 | 53 | M | 11.5 | 4.36 | 3.87 | benign prostate hyperplasia patient | | |
| b12 | 59 | M | 12.6 | 1.75 | 1.53 | benign prostate hyperplasia patient | | |
| b13 | 63 | M | 11.6 | 3.45 | 3.15 | benign prostate hyperplasia patient | | |
| b14 | 64 | M | 16.3 | 10.1 | 7.83 | benign prostate hyperplasia patient | | |
| b15 | 46 | M | 7.5 | 4.29 | 3.87 | benign prostate hyperplasia patient | | |
| b16 | 44 | M | 15.9 | 2.07 | 1.77 | benign prostate hyperplasia patient | | |
| b17 | 59 | M | 13 | 2.16 | 1.86 | benign prostate hyperplasia patient | | |
| b18 | 58 | M | 10.2 | 2.05 | 1.84 | benign prostate hyperplasia patient | | |
| c1 | 40 | M | 9.1 | 1.59 | 1.28 | prostate cancer patient | 2c | 6 |

TABLE 1-continued

Relevant data of the PSA expression in the serum sample of the patients shown and detected in FIG. 10.

| Group | age | gender | free PSA (%) | PSA | cPSA | serum | tumor tages | Gleason score |
|---|---|---|---|---|---|---|---|---|
| c2 | 74 | M | | 444 | 239.8 | prostate cancer patient | | 8 |
| c3 | 71 | M | 11.5 | 8.73 | 7.27 | prostate cancer patient | | 7 |
| c4 | 67 | M | 8.2 | 4.74 | 4.51 | prostate cancer patient | | 6 |
| c5 | 58 | M | | 47.6 | 41.95 | prostate cancer patient | | 8 |
| c6 | 54 | M | 7.5 | 3.88 | 3.4 | prostate cancer patient | | 6 |
| c7 | 73 | M | 12.2 | 5.82 | 4.76 | prostate cancer patient | | 7 |
| c8 | 59 | M | 9.7 | 2.16 | 1.84 | prostate cancer patient | 2c | 7 |
| c9 | 63 | M | 20.1 | 7.68 | 5.71 | prostate cancer patient | | 7 |
| c10 | 69 | M | 5.9 | 9.93 | 9.17 | prostate cancer patient | | 6 |
| c11 | 67 | M | 16.2 | 11.7 | 9.66 | prostate cancer patient | 3a | 7 |
| c12 | 54 | M | 17.4 | 1.78 | 1.34 | prostate cancer patient | 2c | 7 |
| c13 | 42 | M | 11.3 | 1.86 | 1.43 | prostate cancer patient | 2a | 6 |
| c14 | 80 | M | 14.1 | 6.71 | 5.66 | prostate cancer patient | | 6 |
| c15 | 60 | M | 15.6 | 4.61 | 3.98 | prostate cancer patient | | 6 |
| c16 | 63 | M | 19.1 | 4.51 | 4.19 | prostate cancer patient | | 7 |
| c17 | 62 | M | 28.7 | 4.98 | 3.71 | prostate cancer patient | 2c | 6 |
| c18 | 71 | M | 24.1 | 13.2 | 11.47 | prostate cancer patient | | 5 |
| c19 | 79 | M | 15.2 | 11.4 | 10.43 | prostate cancer patient | | 8 |
| c20 | 76 | M | 10.7 | 4.91 | 4.54 | prostate cancer patient | | 6 |
| m1 | 69 | M | | >50 | | prostate cancer metastasis patient | | |
| m2 | 86 | M | | >50 | | prostate cancer metastasis patient | | |
| m3 | 60 | M | | >50 | | prostate cancer metastasis patient | | |
| m4 | 67 | M | | >50 | | prostate cancer metastasis patient | | |
| m5 | 72 | M | | 2000 | | prostate cancer metastasis patient | | |
| m6 | 75 | M | | 1875 | | prostate cancer metastasis patient | | |
| m7 | 70 | M | | 216 | | prostate cancer metastasis patient | | |
| m8 | 61 | M | | 500 | | prostate cancer metastasis patient | | |
| m9 | 63 | M | | 104 | 51.35 | prostate cancer metastasis patient | | |
| m10 | 56 | M | | 2853 | 2712 | prostate cancer metastasis patient | | |
| m11 | 52 | M | | 8076 | 5488 | prostate cancer metastasis patient | | |
| m12 | 75 | M | | 96.9 | 33.93 | prostate cancer metastasis patient | | |
| m13 | 80 | M | | 1570 | 1433 | prostate cancer metastasis patient | | |
| m14 | 71 | M | | 1363 | 1133 | prostate cancer metastasis patient | | |
| m15 | 62 | M | | 229 | 162.2 | prostate cancer metastasis patient | | |
| m16 | 83 | M | | 320 | 238.9 | prostate cancer metastasis patient | | |
| m17 | 71 | M | | 1513 | 1467 | prostate cancer metastasis patient | | |
| f1 | 16 | F | | | | | | |
| f2 | 58 | F | | | | | | |
| f3 | 46 | F | | | | | | |
| f4 | 54 | F | | | | | | |
| f5 | 28 | F | | | | | | |
| f6 | 58 | F | | | | | | |
| f7 | 46 | F | | | | | | |
| f8 | 22 | F | | | | | | |
| f9 | 63 | F | | | | | | |
| f10 | 14 | F | | | | | | |
| f11 | 49 | F | | | | | | |
| f12 | 38 | F | | | | | | |

Thus, the present invention provides a unique and useful EECP gene (and protein), having the nucleotide and encoded amino acid sequence as shown in FIGS. 1, 2 and 3. The present invention provides nucleotide probes corresponding to all or part of the EECP cDNA sequences disclosed herein which may be used to isolate or identify other cDNAs encoding all or part of the EECP gene sequences. The present invention further provides primers capable of specifically amplifying the EECP gene or its RNA transcript. The present invention further provides isolated polynucleotides containing coding sequences of the EECP gene product(s). Such polynucleotides may be used to express EECP encoded protein and peptide having a number of uses. EECP gene probes and primers may also be used to detect the presence or absence of EECP mRNA in various biological samples, for detecting the expression or lack of EECP in prostate cancer cells and other cells, for preparing tumor vaccines, and for molecular diagnostic and prognostic assaying for prostate cancer and breast cancer. Polynucleotides corresponding or complementary to the EECP gene can be useful in methods for treating prostate cancer and/or breast cancer and the metastasis of prostate cancer and breast cancer, such as, for example, in modulating EECP amount and/or biological activity.

More specifically, an EECP polynucleotide useful in the practice of the present invention can comprise a polynucleotide having the nucleotide sequence of human EECP as shown in FIG. 1 (SEQ ID NO: 1), or any aforesaid polynucleotide fragments. Another embodiment comprises a polynucleotide, which encodes the first 30 amino acids of the EECP protein, sequence as shown in FIG. 1 (SEQ ID NO: 2), a sequence complementary thereto, or a polynucleotide fragment thereof. Another embodiment comprises a polynucleotide capable of hybridizing under stringent hybridization conditions to the EECP cDNA shown in FIG. 1 (SEQ ID NO: 1) or to a polynucleotide fragment thereof.

A typical embodiment of EECP polynucleotide is a EECP polynucleotide having the sequence shown in FIG. 1. EECP polynucleotide can comprises a polynucleotide having the nucleotide sequence of human EECP as shown in FIG. 1, wherein T can also be U; a polynucleotide that encodes all or part of the EECP protein; a sequence complementary to the foregoing; or any aforesaid polynucleotide fragment. Another embodiment comprises a polynucleotide having the sequence as shown in FIG. 1, from nucleotide residue number 18 through nucleotide residue number 644, wherein T can also be U.

Typical embodiments of the present invention disclosed herein include EECP polynucleotides containing specific portions of the EECP mRNA sequence (and those complementary to such sequences), such as those encoding the protein and fragments thereof. For example, representative embodiments of the present invention disclosed herein include: polynucleotides encoding about amino acid 1 to about amino acid 10 of the EECP protein shown in FIGS. 1 and 3, polynucleotides encoding about amino acid 10 to about amino acid 20 of the EECP protein shown in FIGS. 1 and 3, polynucleotides encoding about amino acid 20 to about amino acid 30 of the EECP protein shown in FIGS. 1 and 3, polynucleotides encoding about amino acid 30 to about amino acid 50 of the EECP protein shown in FIGS. 1 and 3, polynucleotides encoding about amino acid 50 to about amino acid 60 of the EECP protein shown in FIGS. 1 and 3, polynucleotides encoding about amino acid 60 to about amino acid 70 of the EECP protein shown in FIGS. 1 and 3, polynucleotides encoding about amino acid 70 to about amino acid 80 of the EECP protein shown in FIGS. 1 and 3, polynucleotides encoding about amino acid 80 to about amino acid 90 of the EECP protein shown in FIGS. 1 and 3, and polynucleotides encoding about amino acid 90 to about amino acid 100 of the EECP protein shown in FIGS. 1 and 3, and the like. Following this scheme, polynucleotides encoding portions of the amino acid sequence of amino acids 100-208 of the EECP protein is a typical embodiment of the present invention. Polynucleotides encoding larger portions of the EECP protein are also contemplated. For example polynucleotides encoding from about amino acid 1 (or 20 or 30 or 40 etc.) to about amino acid 20 (or 30, or 40 or 50 etc.) of the EECP protein shown in FIGS. 1 and 3 can be generated by a variety of techniques well known in the art.

Additional illustrative embodiments of EECP polynucleotides include embodiments consisting of polynucleotides having the sequence as shown in FIG. 1 from about nucleotide residue number 1 through about nucleotide residue number 107, from about nucleotide residue number 110 through about nucleotide residue number 330, from about nucleotide residue number 330 through about nucleotide residue number 530, from about nucleotide residue number 530 through about nucleotide residue number 640, from about nucleotide residue number 640 through about nucleotide residue number 768. Additional illustrative embodiments of the present invention disclosed herein include EECP polynucleotide fragments encoding one or more of the biological motifs contained within the EECP protein sequence and discussed below.

Included within the present invention are genomic DNA, cDNAs, ribozymes, and antisense molecules, as well as nucleic acid molecules based on an alternative backbone or including alternative bases, whether derived from natural sources or synthesized. For example, antisense molecules can be RNAs or other molecules, including peptide nucleic acids (PNAs) or non-nucleic acid molecules such as phosphorothioate derivatives, which specifically bind DNA or RNA in a base pair-dependent manner. A skilled artisan can readily obtain these classes of nucleic acid molecules using the EECP polynucleotides and polynucleotide sequences disclosed herein. For example, antisense technology entails the administration of exogenous oligonucleotides that bind to a target polynucleotide located within the cells. The term "antisense" refers to the fact that such oligonucleotides are complementary to their intracellular targets, e.g., EECP. See for example, Jack Cohen, 1988, *OLIGODEOXYNUCLEOTIDES, Antisense Inhibitors of Gene Expression, CRC Press; and Synthesis* 1:1-5 (1988). The EECP antisense oligonucleotides of the present invention such as, for example, S-oligonucleotides derivatives (phosphorothioate derivatives or S-oligos, see, Jack Cohen, supra), exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention may be prepared by treatment of the corresponding O-oligos with 3H-1,2-benzodithiol-3-one-1,1-dioxide, which is a sulfur transfer reagent. See Iyer, R. P. et al, 1990, *J. Org. Chem.* 55:4693-4698; and Iyer, R. P. et al., 1990, *J. Am. Chem. Soc.* 112:1253-1254, the disclosures of which are fully incorporated by reference herein.

Further specific embodiments of this aspect of the present invention include primers and primer pairs, which allow the specific amplification of the polynucleotides of the present invention or of any specific parts thereof, and probes that selectively or specifically hybridize to nucleic acid molecules of the present invention or to any part thereof. Probes may be labelled with a detectable marker, such as, for example, radioisotope, fluorescent compound, bioluminescent compound, chemiluminescent compound, metal chelator or enzyme. Such probes and primers can be used to detect the presence of EECP polynucleotide in a sample and as a means for detecting the cell expressing EECP protein. An example of such probe is a polynucleotide comprising all or part of the human EECP cDNA sequence shown in FIG. 1 (SEQ ID NO: 1 and 2). Examples of primer pairs capable of specifically amplifying EECP mRNAs are also described in the Examples which follow. As will be understood by the skilled artisan, a great many different primers and probes can be prepared based on the sequences provided herein and used effectively to amplify, clone and/or detect the EECP mRNA.

The EECP polynucleotides of the present invention are useful for a variety of purposes, including but not limited to their use as probes and primers for the amplification and/or detection of the EECP gene, mRNA, or fragments thereof; as reagents for the diagnosis and/or prognosis of prostate and colon cancer; as coding sequences capable of directing the expression of EECP polypeptides; as tools for modulating or inhibiting the expression of the EECP gene and/or translation of the EECP transcript; and as therapeutic agents.

The present invention also provides EECP protein and polypeptides which may be used, for example, to generate antibodies to various portions of EECP such as the membrane associated and secreted fragments. In the polypeptide sequence shown in FIG. 2 (SEQ ID NO: 3 and 4), polypeptides that can be used to generate antibodies to any portion of the EECP protein including, for example: a polypeptide containing at least 6 amino acids of the EECP sequence shown in FIG. 2.

Polypeptides that can be used in practicing the present invention (e.g. as immunogens or as modulators of invasion) typically consist of a polypeptide containing at least 6 amino acids of the EECP sequence shown in FIG. 2, including the lysine at position 11; a polypeptide containing at least 6 amino acids of the EECP sequence shown in FIG. 2 including the valine at position 24; a polypeptide containing at least 6 amino acids of the EECP sequence shown in FIG. 2 including the glutamic acid at position 68; a polypeptide containing at least 6 amino acids of the EECP sequence shown in FIG. 2 including the isoleucine at position 119; a polypeptide containing at least 6 amino acids of the EECP sequence shown in FIG. 2 including the glycine at position 150; and/or a polypeptide containing at least 6 amino acids of the EECP sequence shown in FIG. 2 including the tryptophan at position 183. Optionally, such illustrative polypeptide embodiments include any one of other amino acids shown in FIG. 2, for example, the methionine at position 1.

Embodiments of the present invention disclosed herein include a various variants of EECP protein such as polypeptides having amino acid insertions, deletions and substitutions. EECP variants can be made using methods known in the art such as site-directed mutagenesis, alanine scanning, and PCR mutagenesis. Site-directed mutagenesis (Carter et al., 1986, *Nucl. Acids Res.* 13:4331; Zoller et al., 1987, *Nucl. Acids Res.* 10:6487), cassette mutagenesis (Wells et al., 1985, *Gene* 34:315), restriction selection mutagenesis (Wells et al., 1986, *Philos. Trans. R. Soc. London Ser. A,* 317:415) or other known techniques can be performed on the cloned DNA to produce the EECP variant DNA. Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is a typical preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins*, (W.H. Freeman & Co., N.Y.); Chothia, 1976, *J. Mol. Biol.,* 150:1). If alanine substitution does not yield adequate amounts of variant, an isosteric amino acid can be used.

As discussed above, embodiments of the claimed invention include polypeptides containing less than 208 amino acid sequences of the EECP protein shown in FIG. 2 (and the polynucleotides encoding such polypeptides). For example, representative embodiments of the present invention disclosed herein include polypeptide consisting of about amino acid 1 to about amino acid 10 of the EECP protein shown in FIG. 2, polypeptide consisting of about amino acid 20 to about amino acid 30 of the EECP protein shown in FIG. 2, polypeptide consisting of about amino acid 30 to about amino acid 40 of the EECP protein shown in FIG. 2, polypeptide consisting of about amino acid 40 to about amino acid 50 of the EECP protein shown in FIG. 2, polypeptide consisting of about amino acid 50 to about amino acid 60 of the EECP protein shown in FIG. 2, polypeptide consisting of about amino acid 60 to about amino acid 70 of the EECP protein shown in FIG. 2, polypeptide consisting of about amino acid 70 to about amino acid 80 of the EECP protein shown in FIG. 2, polypeptide consisting of about amino acid 80 to about amino acid 90 of the EECP protein shown in FIG. 2 and polypeptide consisting of about amino acid 90 to about amino acid 100 of the EECP protein shown in FIG. 2, and the like. Following this scheme, polypeptides consisting of portions of the amino acid sequence of amino acids 100-208 of the EECP protein are typical embodiments of the present invention. Polypeptides consisting of larger portions of the EECP protein are also contemplated. For example polypeptide consisting of about amino acid 1 (or 20 or 30 or 40 etc.) to about amino acid 20, (or 30, or 40 or 50 etc.) of the EECP protein shown in FIG. 2 can be generated by a variety of techniques well known in the art.

Antibodies capable of specifically binding to and identifying EECP protein or polypeptides can be used to detect the loss and/or presence of the secreted EECP and/or EECP expressing cells in any biological sample, to determine its level in the blood circulation, subcellular location, detect and image prostate and/breast cancer cells and prostate and/or breast tumors, and modulate or inhibit EECP biological activity. Antibodies may also be used therapeutically as described further below. Methods for generating polyclonal and monoclonal antibodies are well known in the art.

The present invention also provides recombinant DNA or RNA molecules containing EECP polynucleotide, including but not limited to phages, plasmids, phagemids, cosmids, YACs, BACs, as well as various viral and non-viral vectors well known in the art, and cells transformed or transfected with such recombinant DNA or RNA molecules. As used herein, a recombinant DNA or RNA molecule is a DNA or RNA molecule that has been subjected to molecular manipulation in vitro. Methods for generating such molecules are well known (see, for example, Sambrook et al, 1989, supra).

The present invention further provides a host-vector system comprising a recombinant DNA molecule containing EECP polynucleotide within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as Sf9 cell). Examples of suitable mammalian cells include various prostate cancer cell lines such as LnCaP, 22RV1, PC-3, DU145, LAPC-4, TsuPr1; breast cancer cell lines such as T47D, MCF7, Hs578T, UACC-812, other transfectable or transducible prostate cancer and breast cancer cell lines, as well as a number of mammalian cells routinely used for the expression of recombinant proteins (e.g., COS, CHO, 293, 293T cells). More particularly, a polynucleotide comprising the coding sequence of EECP can be used to generate EECP protein or fragments thereof using any number of host-vector systems routinely used and widely known in the art.

A wide range of host-vector systems suitable for the expression of EECP protein or fragments thereof are available, see for example, Sambrook et al., 1989, *Current Protocols in Molecular Biology,* 1995, supra. Preferred vectors for mammalian expression include but are not limited to pSG5, pcDNA 3.1 myc-His-tag (Invitrogen), the retroviral vector pSR.alpha.tkneo (Muller et al., 1991, *MCB* 11:785) and/or the Tag5 vector (GenHunter Corporation, Nashville Tenn.). Using these expression vectors, EECP may be more suitable for being expressed in several prostate and non-prostate cancer cell lines, including for example 3T3, 293, 293TPC-3, LNCaP and TsuPr1. The host-vector systems of the present invention are useful for the production of EECP protein or fragment thereof. Such host-vector systems may be employed to study the functional properties of EECP and EECP mutations.

In addition to the detection of dysregulated cell growth, proteins encoded by the EECP gene or fragments thereof, will have a variety of uses, including but not limited to methods for generating antibodies and identifying ligands and other agents and cellular constituents that bind to EECP gene products. Such proteins may also be used as cancer vaccines. Antibodies raised against EECP protein or fragment thereof may be useful in diagnostic and prognostic assays, imaging methodologies (including, particularly, cancer imaging), and therapeutic methods in the management of human cancers characterized by the loss and/or increased expression of EECP protein, such as prostate and breast cancers. Various immunological assays useful for the detection of EECP protein are contemplated, including but not limited to various types of radioimmunoassays, enzyme-linked immunosorbent assays (ELISA), enzyme-linked immunofluorescent assays (ELIFA), immunocytochemical methods, etc. Such antibodies may be labeled and used as immunological imaging reagents capable of detecting prostate and/or breast cells (e.g., in radioscintigraphic imaging methods).

In a specific embodiment, a novel EECP protein having the amino acid sequence of human EECP is provided in FIG. 2 (SEQ ID NO: 3). Fusion proteins which combine all or part of EECP with a heterologous polypeptide are also contemplated and a representative embodiment takes the glutathione-s-synthetase transferase as the heterologous polypeptide. In another typical embodiment, the chimeric molecule may comprise a fusion of the EECP with an immunoglobulin or a particular region of an immunoglobulin. For a bivalent form of the chimeric molecule (also referred to as "immunoadhesin"), such a fusion could be directed to the Fc region of an IgG molecule. Suitable Ig fusions include the substitution of a soluble (transmembrane domain deleted or inactivated) form of EECP polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. A variety of fusion polypeptides are well known in the art and typical embodiments are described in *Current Protocols In Molecular Biology, Units 9 and 16*, Frederick M. Ausubul et al. eds., 1995.

The EECP protein of the present invention can be embodied in many forms, preferably in isolated form. As used herein, the protein is said to be "isolated" when physical, mechanical or chemical methods are employed to remove the EECP protein from cellular constituents, cellular secretions and human body fluid that are normally associated with the protein. A skilled artisan can readily employ standard purification methods to obtain an isolated EECP protein. A purified EECP protein molecule will be substantially free of other proteins or molecules which impair the binding of EECP to antibodies or other ligands. The nature and degree of isolation and purification will depend on the intended use. Embodiments of the EECP protein include a purified EECP protein and a functional, soluble EECP protein. Likewise, such functional, soluble EECP protein or fragments thereof have the ability to bind antibodies, ligands and/or use as a proteinase substrate.

Nucleic acids that encode EECP or its modified forms can also be used to generate either transgenic animals or "knock out" animals (or cell lines) which, in turn, are useful in developing and screening of therapeutically useful reagents. A transgenic animal (e.g., mouse or rat) is an animal having cells that contain a transgene, said transgene is introduced into the animal or an ancestor of the animal at a prenatal, e.g., an embryonic stage. A transgene is a DNA that is integrated into the genome of a cell from which a transgenic animal develops. In one embodiment, EECP-encoding cDNA can be used to clone genomic DNA encoding EECP in accordance with the established techniques and the genomic sequences used to generate transgenic animals that contain cells expressing DNA encoding EECP. Methods for generating transgenic animals, particularly animals such as mice or rats, have become conventional in the art and are described, for example, in U.S. Pat. Nos. 4,736,866 and 4,870,009. Typically, EECP transgene incorporating with tissue-specific enhancers would target to particular cells. Transgenic animals that include a copy of transgene encoding EECP introduced into the germ line of the animal at an embryonic stage can be used to examine the effect of increased expression of DNA encoding EECP. Such animals can be used as tester animals for reagents thought to confer protection from, for example, pathological conditions associated with its overexpression. In accordance with this aspect of the present invention, an animal is treated with the reagent and a reduced incidence of the pathological condition, compared to untreated animals bearing the transgene, would indicate a potential therapeutic intervention for the pathological condition.

In another aspect, non-human homologues of EECP may be used to construct a EECP "knock out" animal that has a defective or altered gene encoding EECP as a result of homologous recombination between the endogenous gene encoding EECP and altered genomic DNA encoding EECP introduced into an embryonic cell of the animal. For example, EECP-encoding cDNA can be used to clone genomic DNA encoding EECP in accordance with established techniques. A portion of the genomic DNA encoding EECP can be deleted or replaced with another gene, such as a gene encoding a selectable marker that can be used to detect the integration. Typically, several kilobases of unaltered flanking DNA (5' and 3' ends) are included in the vector (for a description of homologous recombination vectors, see e.g., Thomas and Capecchi, 1987, *Cell* 51:503). The vector is introduced into an embryonic stem cell line (e.g., by electroporation) and cells in which the introduced DNA has homologously recombined with the endogenous DNA are selected (see e.g., Li et al., 1992, *Cell* 69:915). The selected cells are then injected into a blastocyst of an animal (e.g., mouse or rat) to form aggregation chimeras (see e.g., Bradley, in Robertson, ed., 1987, *Teratocarcinomas and Embryonic Stem Cells: A Practical Approach*, (IRL, Oxford), pp. 113-152). A chimeric embryo can then be implanted into a suitable pseudopregnant female foster animal and the embryo finally becomes a "knock out" animal. Progeny harboring the homologously recombined DNA in their germ cells can be identified by standard techniques and used to breed animals in which all cells contain the homologously recombined DNA. Knockout animals can be characterized for instance, by their ability to defend against certain pathological conditions and by their development of pathological conditions due to the absence of EECP polypeptide.

Recombinant methods may be used to generate nucleic acid molecules encoding the EECP protein. In this regard, the EECP-encoding nucleic acid molecules described herein provide means for generating EECP protein and fragments thereof. Such EECP polypeptides are particularly useful in generating domain specific antibodies (e.g., antibodies recognizing a predominantly secreted or predominantly membrane associated epitope of the EECP protein), identifying substances or cellular factors that bind to a particular EECP domain, and in various therapeutic contexts, including but not limited to cancer vaccines. EECP polypeptides containing this particularly interesting structure can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity.

Another aspect of the present invention provides antibodies that immunospecifically bind to the EECP protein and polypeptide fragments thereof. The most preferred antibodies will selectively bind to EECP protein and will not bind (or will bind weakly) to non-EECP proteins and polypeptides. Major anti-EECP antibodies include monoclonal and polyclonal antibodies as well as fragments containing the antigen binding domain and/or one or more complementary determining regions of these antibodies. As used herein, an antibody fragment is defined as at least a portion of the variable region of the immunoglobulin molecule which binds to the target molecule, i.e., the antigen binding region.

For some applications, it may be desirable to generate antibodies which specifically react with a particular EECP protein and/or an epitope within a particular structural domain. For example, preferred antibodies useful for cancer diagnostic imaging purposes are those which react with an epitope in a membrane associated region of the EECP protein as expressed in cancer cells. Such antibodies may be generated by using the EECP protein, or using peptides derived from secreted or other domains of EECP, and used as an immunogen.

The EECP antibodies of the present invention are particularly useful in prostate and breast cancer diagnostic and prognostic assays, imaging methodologies, and therapeutic strategies. The present invention provides various immunological assays for detecting and quantifying EECP. Such assays generally comprise one or more EECP antibodies capable of recognizing and binding EECP, and can be performed within various immunological assays well known in the art, including but not limited to various types of radioimmunoassays, enzyme-linked immunosorbent assays (ELISA), enzyme-linked immunofluorescent assays (ELIFA), and the like. In addition, the present invention also provides immunological imaging methods capable of detecting prostate cancer, including but not limited to radioscintigraphic imaging methods using labeled EECP antibodies. Such assays may be clinically used for detecting, monitoring, and prognosticating prostate and/or breast cancer, particularly advanced prostate and/or breast cancer.

EECP antibodies may also be used in methods for purifying EECP protein and polypeptides and for isolating EECP homologues and related molecules. For example, in one embodiment, the method for purifying EECP protein comprises incubating EECP antibody, which has been coupled to a solid matrix, with lysate or other solution containing EECP under conditions which permit the EECP antibody to bind to EECP; washing the solid matrix to eliminate impurities; and eluting the EECP from the coupled antibody. Other uses of the EECP antibodies of the present invention include generating anti-idiotypic antibodies that can mimic the EECP protein.

EECP antibodies may also be used to for example, modulate or inhibit the amount of EECP protein and/or the biological activity of EECP protein or target the cells (such as prostate and/or breast cancer cells) which destroy the lost, or increase of the EECP protein expression. Antibody therapy of prostate and/or breast cancer is described in further detail below. A typical embodiment of the present invention in this context consists of a method for inhibiting the growth of a precancerous or cancerous cell that expresses EECP, comprising contacting the EECP expressed by the neoplastic cell with an effective amount of anti-EECP antibody so that the growth of the neoplastic cell is inhibited. Preferably, the antibody used in this method recognizes a EECP epitope that is predominantly cell surface associated. Methods for antibody mediated inhibition and cell lysis are well known in the art and include, for example, complement-mediated or antibody-dependent cell cytotoxicity (ADCC). An alternative embodiment of the present invention is a method for modulating the biological activity of secreted EECP, comprising contacting the secreted EECP to an effective amount of anti-EECP antibody so that the activity of secreted EECP is modulated. Preferably, the antibody used in this method recognizes a EECP epitope that is predominantly secreted.

Various methods for preparing antibodies are well known in the art. For example, antibodies may be prepared by immunizing a suitable mammalian host using EECP protein, peptide, or fragments, in isolated or immunoconjugated manner (*Antibodies: A Laboratory Manual*, CSH Press, Eds., Harlow, and Lane (1988); Harlow, *Antibodies*, Cold Spring Harbor Press, NY (1989)). In addition, fusion proteins of EECP may also be used, such as EECP GST-fusion protein. In a particular embodiment, a GST fusion protein comprising all or most of the open reading frame amino acid sequence of FIG. 2 can be produced and then used as an immunogen to generate appropriate antibodies. Such GST fusion may be used to prepare several monoclonal and/or polyclonal antibodies capable of immunospecifically reacting with EECP. Cells expressing or overexpressing EECP may also be used for immunizations. Similarly, any cell engineered to express EECP may be used. This strategy may result in the production of monoclonal antibodies and polyclonal antibodies with enhanced capacities for recognizing endogenous EECP.

The amino acid sequence of EECP as shown in FIG. 2 (SEQ ID NO: 3 and 4) may be used to select specific regions of the EECP protein functioning as immunogens. For example, hydrophobicity and hydrophilicity analyses for the EECP amino acid sequence may be used to identify hydrophilic regions in the EECP structure. Regions of the EECP protein that show immunogenic structure, as well as other regions and domains, may readily be identified using various other methods known in the art, such as Chou-Fasman, Garnier-Robson, Kyte-Doolittle, Eisenberg, Karplus-Schultz or Jameson-Wolf analysis. For example, antibodies that preferentially target a specific EECP and fragment thereof can be generated.

Methods for preparing a protein or polypeptide for using as an immunogen and for preparing immunogenic conjugates of a protein with a carrier such as BSA, KLH, or other carrier proteins are well known in the art. In certain circumstances, direct conjugation using, for example, carbodiimide reagents may be used; in other instances, linking reagents such as those supplied by Pierce Chemical Co., Rockford, Ill., is effective. Administration of EECP immunogen is conducted generally by injection over suitable time periods and using suitable adjuvants, as is generally understood in the art. During the immunization schedule, titers of antibodies may be used to determine whether the antibody formation is adequate.

As mentioned above, EECP protein can be or comprise an epitope-bearing portion of the polypeptide encoded by a nucleic acid sequence comprising SEQ ID NO: 1. Such EECP protein may be used to create antibodies using standard immunological techniques. Polyclonal or monoclonal antibodies to the protein or an epitope thereof may be made and used in immunoassays by any of a number of methods known in the art. The epitope refers to an antigenic determinant of a polypeptide. An epitope could comprise 3 amino acids in a spatial conformation which is unique to the epitope. Generally, an epitope consists of at least 5 such amino acids. Methods for determining the spatial conformation of amino acids are known in the art, and include, for example, x-ray crystallography and 2-dimensional nuclear magnetic resonance.

One approach for preparing antibodies to a protein is selecting and preparing an amino acid sequence of all or part of the protein, chemically synthesizing the sequence and injecting it into an appropriate animal, usually a rabbit or a mouse.

Oligopeptides may be selected as candidates for the production of an antibody to the EECP protein, especially the oligopeptides lying in hydrophilic regions, which are more likely to be exposed in the mature protein. Peptide sequence used to prepare antibodies against any fragment of EECP is typically at least 5-6 amino acids in length, optionally fused to an immunogenic carrier protein, e.g. KLH or BSA. Additional oligopeptides can be determined using, for example, the Antigenicity Index, Welling, G. W. et al., *FEBS Lett.* 188:215-218 (1985), which is incorporated herein by reference.

Anti-EECP monoclonal antibodies are preferred and can be produced by various means well known in the art. For example, immortalized cell lines which secrete a desired monoclonal antibody can be prepared using the standard method of Kohler and Milstein or modifications which effect immortalization of lymphocytes or spleen cells, as is generally known. The immortalized cell lines secreting the desired antibodies are screened by immunoassay in which the antigen is the EECP protein or EECP fragment. When the appropriate immortalized cell culture secreting the desired antibody is identified, the cells can be expanded and the antibodies can be produced either from in vitro cultures or from ascites fluid.

The antibodies or fragments can also be produced, using current technology, by recombinant methods. Regions that bind specifically to the desired regions of the EECP protein can also be produced by chimeric or CDR grafted antibodies of multiple species origin. Humanized or human EECP antibodies may also be produced. Approaches for producing such humanized antibodies are known, and include chimeric and CDR grafting methods; methods for producing fully human monoclonal antibodies include phage display and transgenic methods (for review, see Vaughan et al., 1998, *Nature Biotechnology* 16: 535-539).

Fully human EECP monoclonal antibodies may be generated using cloning technologies employing large human Ig gene recombinatorial libraries (e.g., phage display) (Griffiths and Hoogenboom, Building an in vitro immune system human antibodies from phage display libraries. *In: Protein Engineering of Antibody Molecules for Prophylactic and Therapeutic Applications in Man.* Clark, M. (Ed.), Nottingham Academic, pp 45-64 (1993); Burton and Barbas, *Human Antibodies from combinatorial libraries. Id., pp* 65-82). Fully human EECP monoclonal antibodies may also be produced using transgenic mice engineered to contain human immunoglobulin gene loci as described in PCT Patent Application WO98/24893 to Kucherlapati et al., published Dec. 3, 1997 (see also Jakobovits, 1998, *Exp. Opin. Invest. Drugs* 7(4): 607-614). This method avoids the in vitro manipulation required with phage display technology and efficiently produces high affinity authentic human antibodies.

Reactivity of EECP antibodies with EECP protein may be established by a number of well known methods, including Western blotting, immunoprecipitation, ELISA, and FACS analyses using, as appropriate, EECP protein, peptides, EECP-expressing cells or extracts thereof.

A EECP antibody or fragments thereof of the present invention can be labeled with a detectable marker or conjugated to a second molecule, such as a cytotoxic or therapeutic agent, and used for targeting a EECP positive cell (Vitetta, E. S. et al., 1993, *Immunotoxin therapy*, in DeVita, Jr., V. T. et al., eds, *Cancer: Principles and Practice of Oncology*, 4th ed., J.B. Lippincott Co., Philadelphia, 2624-2636). A variety of suitable diagnostic and therapeutic conjugates are well known in the art and include, but not limited to, a radioisotope such as an "alpha" emitter, a fluorescent compound, a bioluminescent compound, a chemiluminescent compound, a metal chelator or a polypeptide such as an enzyme. Typical conjugates are described for example in *Current Protocols In Molecular Biology, Units* 11 *and* 17, Frederick M. Ausubul et al. eds., 1995. In preferable embodiments of the present invention, the diagnostic and therapeutic conjugates are coupled to an antibody which recognizes a EECP epitope that is predominantly cell-surface associated.

Typical specific embodiments of the antibodies of the present invention are described: hybridomas are generated which produce the monoclonal antibodies designated 5D5 (IgG1, K), 3C3 (IgG2b), 6B10 (IgG2a, K), 2G3 (IgG1), 4E10 (IgG1, 2b), 10F6 (IgG1, K) and 6F10 (IgG1, K). Therefore specific antibody embodiments of the present invention include a monoclonal antibody, the epitope combining site of which competitively inhibits essentially all of the epitope binding of monoclonal antibody 1F9, 2D10, 2F8, 6B11, 3G3, 8C6 and/or 9G8. Related specific embodiments of the present invention include an immunoconjugate comprising a molecule containing the antigen-binding region of the 5D5, 3C3, 6B10, 2G3, 4E10, 10F6 and 6F10. Monoclonal antibodies 5D5, 3C3, 6B10, 2G3, 4E10, 10F6 and 6F10 are combined to a diagnostic or therapeutic agent.

Additional specific embodiments of the present invention which utilize the polyclonal antibodies and monoclonal antibodies designated 5D5, 3C3, 6B10, 2G3, 4E10, 10F6 and 6F10 include methods for detecting dysregulated cell growth such as cancer by determining the loss or increase of the presence of EECP epitope in a sample from a mammal, comprising reacting a monoclonal antibody with EECP epitope present in the sample, identifying the antibody by immunological binding to a EECP epitope. Said polyclonal antibodies and monoclonal antibodies have an antigen combining site which competitively inhibits the immunospecific binding of an antibody designated 5D5, 3C3, 6B10, 2G3, 4E10, 10F6 and 6F10 and produced by a hybridoma respectively to its target antigen. Additional specific embodiments of the present invention which utilize the polyclonal antibodies and monoclonal antibodies designated 5D5, 3C3, 6B10, 2G3, 4E10, 10F6 and 6F10 include methods for inhibiting the progression of dysregulated cell growth such as cancer, comprising contacting a EECP epitope with a monoclonal antibody or antigen-binding fragment so that the progression of the cancer is inhibited, wherein said monoclonal antibody or antigen-binding fragment has an antigen-binding region of mice monoclonal antibody 5D5, 3C3, 6B10, 2G3, 4E10, 10F6 and 6F10.

Additional specific embodiments of the present invention which utilize the polyclonal and monoclonal antibodies include methods for determining the presence of dysregulated cell growth such as cancer in a biological sample comprising contacting a specimen of said sample with a polyclonal and/or monoclonal antibody or antigen-binding fragment thereof that specifically binds to a EECP epitope, wherein said monoclonal antibody or antigen-binding fragment has an antigen-binding region of mice monoclonal antibody 5D5, 3C3, 6B10, 2G3, 4E10, 10F6 and 6F10 and detecting the binding of said antibody or fragments to said biological sample.

As discussed in detail below, additional specific embodiments of the present invention which utilize the monoclonal antibodies designated 5D5, 3C3, 6B10, 2G3, 4E10, 10F6 and 6F10 include methods for inhibiting dysregulated cell growth such as cancer in a biological sample comprising contacting a specimen of said sample with a monoclonal antibody or antigen-binding fragment thereof that specifically binds to a EECP epitope, wherein said monoclonal antibody or antigen-binding fragment has an antigen-binding region of mice monoclonal antibody 5D5, 3C3, 6B10, 2G3, 4E10, 10F6 and 6F10 so that dysregulated cell growth is inhibited.

Additional illustrative diagnostic methods of the present invention are provided below. These methods merely represent typical embodiments of the present invention described herein and do not limit the present invention in anyway.

Illustrative Diagnostic Methods of the Invention

As mentioned above, assays that evaluate the status of EECP (e.g. the status of the EECP gene and gene products such as mRNAs and proteins) in an individual may be used to provide information on the growth or oncogenic potential of cells from the individual. In particular, the finding that EECP protein mostly lost about 95% of its normal level ("basal-level of male") in plasma of prostate cancer patients, in contrast, the protein is highly expressed (compare to its "basal-level of female") in plasma (serum) of breast cancer patients, therefore, the skilled artisan can use this gene and its products to evaluate the targets suspected of having a disease associated with alterations in the status of EECP.

EECP is expressed in various prostate cancer and breast cancer cell lines. Its level in plasma (serum) is dramatically lower than the "basal level of male" in prostate cancer patients, but higher than the "basal level of female" in breast cancer patients. Because of those features discussed above, the expression status of EECP can provide information useful for determining information including the presence, stage and location of hyperplasia, precancerous and cancerous cells, prognosting and/or predicting tumor aggressiveness. Consequently, an important aspect of the present invention directs to various molecular prognostic and diagnostic methods for examining the status of EECP in biological samples from individuals suffering from, or suspected of suffering from a pathology characterized by dysregulated cellular growth such as cancer. Oncogenesis is known to be a multi-step process where cellular growth becomes progressively dysregulated and cells progress from a normal physiological state to precancerous and then cancerous states (see e.g. Alers et al., Lab Invest. 77(5): 437-438 (1997) and Isaacs et al., Cancer Surv. 23: 19-32 (1995)). Accordingly, examining a biological sample for the evidence of growing a dysregulated cell (such as EECP expression level in prostate and breast cancers) can allow the early detection of such aberrant cellular physiology before a cancer has progressed to a stage at which therapeutic options are more limited. In such examinations, the status of EECP in a biological sample of interest (such as one suspected of having dysregulated cell growth) can be compared, for example, with the status of EECP in a corresponding normal sample (e.g. a sample from the individual that is not effected by a pathology or alternatively another individual not suspected of having dysregulated cell growth) with the alterations in the status of EECP in the biological sample of interest (as compared to the normal sample) providing evidence of dysregulated cellular growth. In addition to using a biological sample that is not effected by a pathology as a normal sample, one can also use a predetermined normative value such as a predetermined normal level of mRNA expression (see e.g. Grever et al., J. Comp. Neurol. 1996 Dec. 9; 376(2):306-14 and U.S. Pat. No. 5,837,501) to compare the EECP in normal versus suspected samples.

The term "status" in this context is used according to its acceptable manner. As specifically described herein, the status of EDCP in a biological sample can be evaluated by examining the sequences of EECP polynucleotide and/or polypeptides in that biological sample. Alternatively, the status of EDCP in a biological sample can be evaluated by examining the levels of EECP gene products (e.g. mRNA and/or proteins) in the biological sample. Alternatively, status of EECP in a biological sample can be evaluated by locating the EECP in normal biological samples and comparing that to the location of EECP in a biological sample suspected of containing evidence of dysregulated cell growth. Alternatively, the status of EECP in a biological sample can be evaluated by observing the presence or absence of a specific EECP species such as the 22 kD protease fragment that results from post-translational autocatalytic cleavage. Alternatively, the status of EDCP in a biological sample can be evaluated by looking for the presence or absence of a specific EECP immunoreactive complex in the biological sample.

Typically, skilled artisans use a number of parameters to evaluate the condition or state of a gene and its products. These include, but are not limited to the integrity and/or methylation pattern of a gene and its regulatory sequences, the location of expressed gene products (including the location of EECP expressing cells), the presence, level, and biological activity of expressed gene products (such as EECP mRNA polynucleotides and polypeptides), the presence or absence of transcriptional and translational modifications to the expressed gene products as well as associations of expressed gene products with other biological molecules such as protein binding partners.

Alterations in the status of EECP may be evaluated by a wide variety of methodologies well known in the art, typically those discussed below. Typically, an alteration in the status of EECP comprises a change in the location of EECP and/or EECP expressing cells, an increase in EECP mRNA and/or protein expression and/or the association or dissociation of EECP with a binding partner. The data as presented herein provides evidence that EECP protein are secreted into plasma (serum) mainly from gland architecture of male genital organs, but upon the disruption of the gland architecture, the EECP protein originally in plasma (serum) are effectively degraded by proteases released into plasma (serum), at that time, a specific representative alteration is a decrease in the levels of the secreted EECP protein in plasma (serum). In contrary, EECP protein is at extremely low level in plasma (serum) of female with normal breast gland with intact histological structure. But it is secreted into plasma (serum) upon disruption of the gland architecture. Because of lacking of potent proteases released into plasma (serum) at the same period from gland of breast, the level of EECP in the said plasma (serum) increases. This is another specific representative alteration in the secreted EECP protein in plasma (serum).

As discussed in detail herein, in order to identify a condition or phenomenon associated with dysregulated cell growth, the status of EECP in a biological sample can be evaluated by a number of methods utilized by skilled artisans including, but not limited to genomic Southern analysis (to examine, for example perturbations in the EECP gene), Northern and/or PCR analysis of EECP mRNA (to examine, for example alterations in the polynucleotide sequences or expression levels of EECP mRNAs), and Western and/or immunohistochemical analysis (to examine, for example alterations in polypeptide sequences, alterations in polypeptide localization within a sample, alterations in expression levels of EECP protein and/or associations of EECP protein with polypeptide binding partners). Detectable EECP polynucleotides include, for example, EECP gene or fragments thereof, EECP mRNA, alternative splice variants EECP mRNAs, and recombinant DNA or RNA molecules containing EECP polynucleotide.

When examining the various EECP species and their ratios in various diagnostic methods, one can also take into account factors such as the localization of the EECP species either within or outside a cell. Such observations are well known in the art and may be undertaken for example by utilizing antibodies specifically directed to domain within secreted species or antibodies specifically directed to a domain associated with the cell surface.

As discussed in detail below, EECP may be analyzed by any one of the wide variety of techniques, including (i) immunohistochemical analysis, (ii) in situ hybridization, (iii) RT-PCR analysis, (iv) Western blotting analysis of clinical samples and cell lines, (v) tissue array analysis, and (vi) in vivo imaging. Illustrative typical protocols for evaluating the status of a gene and its products can be found, for example in *Current Protocols In Molecular Biology*, Units 2 *[Northern Blotting]*, 4 *[Southern Blotting]*, 15 *[Immunoblotting] and* 18 *[PCR Analysis]*, Frederick M. Ausubul et al. eds., 1995. Various specific immunological assays useful for detecting EECP protein include but are not limited to various types of radio-immunoassays, enzyme-linked immunosorbent assays (ELISA), enzyme-linked immunofluorescent assays ELIFA), immunocytochemical methods, and the like. As an example, EECP antibodies may be labeled and used as immunological imaging reagents capable of detecting prostate and breast cancer cells (e.g., in radioscintigraphic imaging methods). For radioscintigraphic in vivo imaging, radiolabeled EECP antibodies specifically reactive with secreted epitopes of EECP are preferred.

Assays for identifying diseases associated with the dysregulation of cell growth and structure disruption such as occurs in prostate and breast cancers may comprise detecting changes of EECP polypeptides or polynucleotides in any one of a wide variety of biological samples to evaluate pathological conditions, such as plasma (serum), urine, stool, semen as well as cell preparations from tissues from the prostate, breast and other tissues which may be effected for example when a cancer metastasizes. Typical samples include peripheral blood and/or plasma (serum) which can be conveniently assayed for the presence of EECP protein or cancer cells, including but not limited to prostate and breast cancers.

Peripheral blood and plasma (serum) may be conveniently assayed for the lost or increased presence of EECP protein and/or prostate or breast cancer cells, using for example, immunological or Northern or RT-PCR analysis to detect EECP. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, *Urol. Res.* 25: 373-384; Ghossein et al., 1995, *J. Clin. Oncol.* 13: 1195-2000; Heston et al., 1995, *Clin. Chem.* 41: 1687-1688). In another approach, a recently described sensitive assay for detecting and characterizing carcinoma cells in blood can be used (Racila et al., 1998, *Proc. Natl. Acad. Sci. USA* 95: 4589-4594). This assay combines immunomagnetic enrichment with multiparameter flow cytometric and immunohistochemical analyses, and is highly sensitive for the detection of cancer cells in blood, reportedly capable of detecting one epithelial cell in 1 ml of peripheral blood.

EECP shares a number of characteristics with prostate specific antigen, including androgen regulation, a presence in plasma (serum), an ability to form a complex with one or more proteins and increased expression levels that are associated with cancer. Consequently, various assays known in the art for evaluating PSA also provide illustrations of typical methods for evaluating EECP. A number of representative assays involving the examination of PSA which may also be used for EECP examination are provided below. Such assays may also be used in combination with assays evaluating the status of EECP.

U.S. Pat. No. 5,840,501, which is incorporated herein by reference, provides typical methods for examining immunologically determinable PSA in a blood sample. In this variation of such well known assays, PSA is examined by a two-site immunometric assays in which the blood sample is treated to render free PSA (fPSA) immunologically non-detectable. Measurement of cPSA blood levels in this context has been found to provide a method for aiding in the diagnosis and monitoring of prostate cancer that is highly sensitive and specific, and eliminates the need for a significant number of patients to undergo unnecessary prostate biopsy. The immunometric assay method described in U.S. Pat. No. 5,840,501 employs three anti-PSA antibodies: an antibody that binds to both cPSA and fpSA (anti-tPSA), a second anti-tPSA antibody which is characterized by the unique property that the binding to fPSA is blocked by the binding of fPSA-specific antibodies, and a third antibody which is a fPSA-specific antibody. Thus, the binding of a fPSA-specific antibody to PSA in the sample allows only cPSA to be measured in the immunometric assay. Following the methods described in U.S. Pat. No. 5,840,501, one skilled in the art could employ analogous methods with, for example three anti-EECP antibodies: an antibody that binds to both cEECP and fEECP (anti-tEECP), a second anti-tEECP antibody which is characterized by the unique property that the binding to FEECP is blocked by the binding of fEECP-specific antibodies, and a third antibody which is a fEECP-specific antibody. Thus, the binding of the fEECP-specific antibody to EECP in the sample would allow only cEECP to be measured in an immunometric assay.

U.S. Pat. No. 5,939,533, which is incorporated herein by reference, provides additional typical immunoassays to measure free PSA as well as proteinase inhibitor complex. In the method described in U.S. Pat. No. 5,939,533, free PSA and PSA complex are measured by a non-competitive immunoassay employing at least two different monoclonal antibodies. The present invention is further characterized in that the PSA proteinase inhibitor complex of interest is formed either with alpha-1-antichymotrypsin, alpha-1-protease inhibitor (API) or alpha-2-macroglobulin. Moreover, the invention described in U.S. Pat. No. 5,939,533 is characterized by the observation that free PSA, the PSA-proteinase inhibitor complex and their ratios can be applied in the diagnosis of patients with prostate cancer. Following the methods described in U.S. Pat. No. 5,939,533, one skilled in the art could employ analogous methods to observe, for example the EECP protein as shown in FIG. 2. In this context, observations of free EECP and/or EECP-protein complex(es) and their ratios may then be applied in the diagnosis of patients with, for example, prostate or breast cancer.

U.S. Pat. No. 5,672,480, which is incorporated herein by reference, provides additional typical immunoassay methods for prostate specific antigen (PSA). Also presented in the method described in U.S. Pat. No. 5,672,480 is a complex which resembles a complex of PSA and alpha. sub. 1-antichymotrypsin (ACT) that can be used as a control in an immunoassay for PSA. U.S. Pat. No. 5,672,480 also proposes methods for isolating polyclonal antibodies from PSA, by partly masking the epitopes that PSA and the polyclonal antibodies binds to isolate the polyclonal antibodies. Following the methods described in U.S. Pat. No. 5,672,480, one skilled in the art could employ the method disclosed in U.S. Pat. No. 5,672,480, use ACT analogues to form a complex with EECP, partly mask the epitopes for the binding of EECP with polyclonal antibodies and isolate anti-EECP polyclonal antibodies by such complex.

U.S. Pat. No. 5,614,372 which is incorporated herein by reference describes another typical bioaffinity assay of prostate-specific antigen (PSA) comprising measuring either the concentration of total PSA (PSA-T), the concentration of free form of PSA (PSA-F) or the concentration of PSA combined to alpha-1-antichymotrypsin (PSA-ACT), PSA-T being the sum of PSA-F and PSA-ACT. According to the disclosure of U.S. Pat. No. 5,614,372, the concentration of another molecule, human glandular kallikrein (hGK-1) is measured additionally. The concentrations of PSA-T and hGK-1 can be measured in one single assay or in separate assays, with the sum of the concentrations of PSA-T and hGK-1 used to determine the ratio a) PSA-F/(PSA-T+hGK-1) and/or b) PSA-ACT/(PSA-T+hGK-1). In the disclosure of U.S. Pat. No. 5,614,372, both of these ratios are shown to have clinical utility for the discrimination of prostate cancer and benign prostatic hyperplasia. Following the methods described in U.S. Pat. No. 5,614,372, one skilled in the art could employ analogous methods to analyze EECP comprising, measuring either the concentration of total EECP (EECP-T), the concentration of free form of EECP (EECP-F) or the concentration of EECP complexed to its binding partner (EECP-BP), EECP-T being the sum of EECP-F and EECP-BP. Additionally, the concentration of human glandular kallikrein (hGK-1) can be measured and used to determine the ratio a) EECP-F/(EECP-T+hGK-1) and/or b) EECP-ACT/(EECP-T+hGK-1). As in the disclosure of U.S. Pat. No. 5,614,372, these ratios can be employed for clinical utility.

U.S. Pat. No. 5,939,258, which is incorporated herein by reference, provides other typical methods for diagnosing breast and prostate micrometastasis whereby isolating nucleic acids from a tissue sample from a patient, amplifying nucleic acids from the tissue sample specific for breast and prostate cancer, or amplifying a signal generated by hybridization of a probe specific to a breast and prostate cancer specific nucleic acid; and detecting the amplified nucleic acids is indicative of micrometastasis of breast and prostate cancer. As illustrated in detail below, probes specific to EECP nucleic acid can similarly be amplified; with the detection of amplified nucleic acids providing evidence of micrometastasis of breast and prostate cancer.

U.S. Pat. No. 5,972,615, which is incorporated herein by reference, provides other typical diagnostic techniques for the detection of human prostate and breast disease. The present invention relates particularly to probes and methods for evaluating the presence and level of RNA sequences that are differentially expressed in metastatic prostate and breast cancer compared to normal human prostate and breast, benign prostatic hyperplasia, and non-metastatic prostate and breast cancer. The present invention also relates to probes and methods for evaluating the presence of RNA sequences that are differentially expressed in the peripheral blood of individuals with the disease state compared to normal healthy individuals. Described are methods of therapeutic use for genes identified as differentially expressed in metastatic prostate cancer, and methods for screening pharmaceuticals effective in treatment of prostate and breast cancer. Similarly, U.S. Pat. No. 5,972,615 provides isolated mammalian nucleic acid molecules encoding alternatively spliced prostate-specific membrane (PSM) antigen, isolated nucleic acid molecules encoding prostate-specific membrane antigen promoter sequences and methods for detecting hematogenous micrometastatic tumor cells of a subject to determine the prostate cancer progression in a subject. As illustrated in detail below, molecules specific for EECP may be used for detecting hematogenous micrometastic tumor cells of a subject to determine the prostate and/or breast cancer progression in a subject.

As illustrated in the various typical embodiments provided below, a wide variety of methods for determining the status of EECP in an individual may be used to provide prognostic and/or diagnostic information. Such methods for determining the status of EECP can provide information useful for predicting susceptibility to a particular disease, the stages and progression of the disease, and/or tumor aggressiveness. Various illustrative aspects of the present invention are provided below as typical methods and assays for determining the status of EECP and evaluating syndromes which involve the dysregulation of the cell growth.

A particularly preferred embodiment of the present invention consists of a method of examining or testing a biological sample of interest for evidence of dysregulated cellular growth comprising comparing the status of EECP in the test biological sample to the status of EECP in a corresponding normal sample, wherein alterations in the status of EECP in the biological sample are associated with disruption of tissue structure and/or dysregulated cellular growth. As the disruption of tissue structure and/or dysregulation of cell growth (i.e. the disruption of normal cellular proliferation that occurs in hyperplasic, precancerous and cancerous cells etc.) is a significant factor in the complex multistep process of carcinogenesis and tumor progression, methods for identifying a condition or phenomena that is indicative of disruption of tissue structure and/or dysregulated cellular growth (e.g., an alteration in the normal biology of EECP) are of particular interest to medical practitioners because the early detection of the pathologic changes of tumor has profound influence on morbidity and mortality.

As discussed in detail below, the plasma (serum) level of EECP exhibits a constellation of characteristics which provide strong evidence that it is involved in oncogenic processes. Consequently, the identification of alterations in the status of EECP in a test sample (e.g. a change of level in plasma/serum) as compared to a corresponding normal sample from, for example an unaffected proximal location (e.g. normal breast or prostate tissue) or an unaffected individual provides evidence of dysregulated cellular growth.

As described in detail above, the status of EECP in a biological sample can be examined by a number of well known procedures in the art. For example, the status of EECP in a biological sample can be examined by comparing, for example, the level of EECP polynucleotide or polypeptide expression known to occur in non-cancerous samples versus precancerous or cancerous samples. After comparing, EECP that can be evaluated includes both the EECP polynucleotide sequence shown in SEQ ID NO: 1 and the EECP polypeptide sequence shown in SEQ ID NO: 3.

A biological sample taken from a specific location in the body can also be examined by evaluating the sample for the presence or absence of EECP expressing cells. This examination can provide evidence of dysregulated cellular growth for example, when EECP expressing cells are found in a biological sample from a region of the body that does not normally contain such cells (such as lymph node, bone or liver etc.), such alterations in the status of EECP in a biological sample are often associated with disruption of tissue structure and/or dysregulated cellular growth. Specifically, one indicator of disruption of tissue structure and/or dysregulated cellular growth is the metastases of cancer cells from an organ of origin (such as the prostate gland or the breast grand) to a different area of the body (such as lymph node). Such evidence of dysregulated cellular growth is important for breast cancer, because an understanding of the distribution of nodal metastasis in breast cancers will make it possible to recognize early recurrent nodal disease (see e.g. *AJR Am J Roentgenol* 1992 October; 159(4):757-61). Such evidence of disruption of tissue structure and/or dysregulated cellular growth is important for prostate cancer, because occult lymph node metastases can be detected in a substantial proportion of patients with prostate cancer, and such metastases are associated with known predictors of disease progression (see e.g. *J Urol* 1995 August; 154(2 Pt 1):474-8).

In a specific embodiment of the present invention, a method for detecting an alteration in the status of EECP mRNA in a biological sample of interest (typically from a patient suspected of having a pathological syndrome exhibiting a constellation of indicators, one of which is high EECP expression) comprises producing cDNA from the sample by reverse transcription using at least one primer; amplifying the EECP cDNA from the cDNA so produced using EECP polynucleotides as sense and antisense primers; and detecting the presence of the amplified EECP cDNA. In a typical embodiment, a method for detecting the EECP gene in a biological sample comprises first isolating genomic DNA from the sample; amplifying the EECP gene from the isolated genomic DNA using EECP polynucleotides as sense and antisense primers; and detecting the presence of the amplified EECP gene. Any number of appropriate sense and antisense probe combinations may be designed from the nucleotide sequence provided for EECP (FIG. 1; SEQ ID NO: 1) and used for amplification. In another embodiment, a method for detecting the presence of EECP protein in a biological sample comprises first contacting the sample with a EECP antibody, a polypeptide containing a EECP epitope binding region, or a recombinant protein containing a EECP epitope binding region, and then detecting the binding of EECP protein in the sample thereto.

Methods for identifying a cell which expresses and/or exhibits aberrant expression of EECP are also provided. In one embodiment, an assay for identifying a cell which expresses EECP gene comprises detecting the presence of EECP mRNA in the cell. Methods for detecting particular mRNA in cells are well known and include, for example, hybridization assays using DNA probes (such as in situ hybridization using labeled EECP riboprobes, Northern blotting and related techniques) and various nucleic acid amplification assays (such as RT-PCR using complementary primers specific for EECP, and other amplification type detection methods, such as, for example, branched DNA, SISBA, TMA and the like). In addition, an assay for identifying a cell which expresses EECP gene comprises detecting the presence of EECP protein in the cell or secreted by the cell. Various methods for detecting proteins are well known in the art and can be employed for detecting EECP protein and EECP expressing cells.

A typical embodiment of the present invention provides assays for determining the presence of cancer in an individual, comprising detecting a significant increase or decrease in EECP mRNA or protein expression in a biological sample relative to the expression levels in the corresponding normal sample. The presence of EECP protein and/or mRNA may, for example, be evaluated in biological samples including but not limited to blood and plasma (serum) as well as tissue samples from colon, prostate, pancreas and breast etc. Moreover, biological samples from tissues and sites associated with cancer metastases can also be evaluated. The presence of significant level changes of EECP expression and/or alterations in EECP in any of these tissues may be useful to indicate the emergence, progression, metastases and/or prognosis of these cancers, since the corresponding normal tissues do not express EECP mRNA or protein or express it at higher (for prostate) or lower (for breast) levels.

A typical embodiment of the present invention provides an assay for determining the presence of dysregulated cell growth and/or disrupted tissue structure (such as occurs in cancer) in an individual, comprising detecting a significant decrease or increase in EECP mRNA or protein expression in a test cell or tissue sample relative to the expression levels in the corresponding normal cell or tissue. The increase of EECP mRNA in a breast sample, for example, may indicate the emergence, progression, metastases and/or prognosis of breast cancer. The status of EECP gene products may also be determined at protein level rather than at nucleic acid level. For example, such a method or assay comprises determining the level of EECP protein expressed by cells in a test tissue sample and comparing it to the level of EECP expressed in a corresponding normal sample. The change in level of EECP protein can be evaluated, for example, using immunohistochemical methods. EECP antibodies or binding partners capable of detecting EECP protein expression may be used in a variety of assays.

As mentioned above, methods for detecting and quantifying the expression of EECP mRNA or protein described herein can use any standard nucleic acid and protein detection and quantification technologies well known in the art. Standard methods for detecting and quantifying EECP mRNA include in situ hybridization using labeled EECP riboprobes, Northern blotting and related techniques using EECP polynucleotide probes, RT-PCR analysis using primers specific for EECP, and other amplification type detection methods, such as, branched DNA, SISBA, TMA and the like. In a specific embodiment, semi-quantitative RT-PCR may be used to detect and quantify EECP mRNA expression. Any number of primers capable of amplifying EECP may be used for this purpose, including but not limited to the various primer sets. Standard methods for detecting and quantifying protein may be used for this purpose. In a specific embodiment, polyclonal or monoclonal antibodies specifically reactive with the EECP protein can be used in an immunohistochemical assay of biopsied tissue.

In related embodiments of the methods described above, one can evaluate the integrity EECP nucleotide and amino acid sequences in a biological sample in order to identify perturbations in the structure of these molecules such as insertions, deletions, substitutions and the like. Such embodiments are useful because perturbations in the nucleotide and amino acid sequences are observed in a large number of proteins associated with a growth dysregulated phenotype (see e.g. Marrogi et al., *J. Cutan. Pathol.* 26(8): 369-378 (1999)). A wide variety of assays for observing perturbations in nucleotide and amino acid sequences are well known in the art. For example, the size and structure of nucleic acid or amino acid sequences of EECP gene products can be observed by the Northern, Southern, Western, PCR and DNA sequencing protocols discussed herein. In addition, other methods for observing perturbations in nucleotide and amino acid sequences such as single strand conformation polymorphism analysis are well known in the art (see e.g. U.S. Pat. Nos. 5,382,510 and 5,952,170).

In another embodiment, one can examine the methylation status of the EECP gene in a biological sample. Aberrant demethylation and/or hypermethylation of CpG islands in gene 5' regulatory regions frequently occurs in immortalized and transformed cells and can result in altered expression of various genes. For example, promoter hypermethylation of the pi-class glutathione S-transferase (a protein expressed in normal prostate but not expressed in >90% of prostate cancer) appears to permanently silence transcription of this gene and is the most frequently detected genomic alteration in prostate cancer (De Marzo et al., *Arm J. Pathol.* 155(6): 1985-1992 (1999)). In addition, this alteration is present in at least 70% of cases of high-differentiated prostatic intraepithelial neoplasia (PN) (Brooks et al, *Cancer Epidemiol. Biomarkers Prev.*, 1998, 7:531-536). In another example, expression of the LAGE-I tumor specific gene (which is not expressed in normal prostate but expressed in 25-50% of prostate cancers) is induced by deoxy-azacytidine in lymphoblastoid cells, suggesting that tumoral expression is due to demethylation (Lethe et al., *Int. J. Cancer* 76(6): 903-908 (1998)). Various assays for examining methylation status of a gene are well known in the art. For example, one can utilize in Southern hybridization approaches methylation-sensitive restriction enzymes which can not cleave sequences containing methylated CpG sites, thereby assess the overall methylation status of CpG islands. In addition, MSP (methylation specific PCR) can rapidly detect the methylation status of all the CpG sites present in a CpG island of a given gene. This procedure involves initial modifying DNA by sodium bisulfite (which converts all unmethylated cytosines to uracil) followed by amplifying DNA using primers specific for methylated versus unmethylated DNA. Protocols involving methylation interference can also be found for example in *Current Protocols In Molecular Biology*, Units 12, Frederick M. Ausubul et al. eds., 1995.

An examination of increased gene amplification expression provides an additional method of assessing the status of EECP. Gene amplification or mRNA transcription can be measured directly in a sample, for example, by conventional Southern blotting, dot blotting (DNA analysis) and in situ hybridization, Northern blotting [Thomas, *Proc. Natl. Acad. Sci. USA*, 77:5201-5205 (1980)], using an appropriately labeled probe, based on the sequences provided herein. In addition, antibodies may be employed to recognize specific duplexes, including DNA duplexes, RNA duplexes, and DNA-RNA hybrid duplexes or DNA-protein duplexes. Therefore, one can label the antibodies bound to the solid surface of the duplex, detect the presence of the antibody bound to the duplex, thereby quantify the specific duplex.

The present invention also directs to predicting susceptibility to developing a syndrome associated with dysregulated EECP expression (such as cancer) in an individual. In one embodiment, a method for predicting susceptibility to cancer comprises detecting EECP mRNA or EECP protein in a biological sample, the change of its expression level indicating susceptibility to cancer. In a specific embodiment, the expression level of EECP in serum or prostate or breast tissue is examined, with the decrease or increase of EECP in the sample indicating the susceptibility of prostate or breast cancer, respectively (or the emergence or existence of prostate or breast tumor). In a closely related embodiment, one can evaluate the integrity EECP nucleotide and amino acid sequences in a biological sample in order to identify perturbations in the structure of these molecules such as insertions, deletions, substitutions and the like, with the presence of one or more perturbations in EECP gene products in the sample providing an indication of cancer susceptibility (or the emergence, existence or metastasis of a tumor).

Yet another related aspect of the present invention is directed to methods for gauging tumor aggressiveness. In one embodiment, a method for gauging aggressiveness of a tumor comprises determining the level of EECP mRNA or EECP protein expressed in plasma (serum), semen, urine, stool etc. or by cells in a sample of the tumor, comparing the level so determined to the level of EECP mRNA or EECP protein expressed in a corresponding normal sample taken from other normal individuals or a normal tissue reference sample from the same individual, wherein the degree of EECP mRNA or EECP protein expression in the suspect sample relative to the normal sample indicates the degree of aggressiveness. In a specific embodiment, the aggressiveness of prostate or breast tumors is evaluated by determining the extent to which EECP is expressed in a sample from an individual, with lower (e.g. prostate cancer and breast cancer) or higher (e.g. breast cancer) expression levels indicating more aggressive tumors. In a closely related embodiment, one can evaluate the integrity EECP nucleotide and amino acid sequences in a biological sample in order to identify perturbations in the structure of these molecules such as insertions, deletions, substitutions and the like, with the presence of one or more perturbations indicating more aggressive tumors.

Yet another related aspect of the present invention is directed to methods for observing the progression of a malignancy in an individual over time. In one embodiment, methods for observing the progression of a malignancy in an individual over time comprise determining the level of EECP mRNA or EECP protein expressed in a biological sample, comparing the level so determined to the level of EECP mRNA or EECP protein expressed in an equivalent biological sample taken from the same individual at a different time, wherein the degree of EECP mRNA or EECP protein expression in the sample over time provides information on the progression of the cancer. In a specific embodiment, the progression of a cancer is evaluated by determining the extent to which EECP expression in the tumor cells alters over time, with lower expression levels indicating a progression of the cancer. In an alternative embodiment, the progression of a cancer is evaluated by determining the extent to which EECP expression in plasma (serum) alters over time, with lower concentrations indicating a progression of prostate cancer, and higher concentrations indicating a progression of breast cancer. In a closely related embodiment, one can evaluate the integrity EECP nucleotide and amino acid sequences in a biological sample so as to identify the perturbations in the structure of these molecules such as insertions, deletions, substitutions and the like, with the presence of one or more perturbations indicating a progression of the cancer.

The above diagnostic approaches can be combined with any one of a wide variety of prognostic and diagnostic protocols known in the art. For example, another embodiment of the present invention disclosed herein is directed to methods for testing a coincidence between the abnormality of EECP gene and EECP gene products and other factors that are associated with malignancy as a means of diagnosing and prognosticating the status of a tissue sample. A wide variety of factors associated with malignancy can be utilized such as the expression of genes associated with malignancy (including PSA, PSCA, PSM and human glandular kallikrein expression) as well as cytological examinations (see e.g. Bocking et al., *Anal Quant Cytol.* 6(2):74-88 (1984); Eptsein, *Hum Pathol.* 1995 February; 26(2):223-9 (1995); Thorson et al., *Mod Pathol.* 1998 June; 11(6):543-51; Baisden et al., *Am J Surg Pathol.* 23(8):918-24 91999)). Methods for testing a coincidence between the expression of the EECP gene and EECP gene products (or abnormality of the EECP gene and EECP gene products) and an additional factor that is associated with malignancy are useful, because the presence of a set or constellation of specific factors that coincide provides information crucial for diagnosing and prognosticating the status of a tissue sample.

In a typical embodiment, methods for observing a coincidence between the expression of EECP gene and EECP gene products and a factor that is associated with malignancy entails detecting the overexpression of EECP mRNA or protein in a biological sample, detecting the overexpression of PSA mRNA or protein in a biological sample, and observing a coincidence of EECP mRNA or protein and PSA mRNA or protein overexpression. In a specific embodiment, the expression of EECP and PSA mRNA in plasma (serum) or prostate and colon tissue is examined. In a preferred embodiment, the coincidence of EECP and PSA mRNA overexpression in the sample provides an indication of prostate or breast cancer, prostate or breast cancer susceptibility or the emergence, existence or metastasis of a prostate or breast tumor.

In these methods, the status of EECP can be examined in a wide variety of biological samples, such as plasma (serum), urine, stool, semen as well as cell preparations from tissues from the prostate, breast and other tissues which may be effected for example when a cancer metastasizes. In addition to these samples, peripheral blood and/or plasma (serum) can be conveniently assayed for the levels of EECP protein or cancer cells, including but not limited to prostate and breast cancers. The status of EECP in the biological sample is evaluated by any one of a large variety of art accepted methods such as Southern analysis, Northern analysis, polymerase chain reaction analysis and immunoassay. Preferably, the biological sample is evaluated by examining the level of EECP mRNA expression or EECP protein expression.

An alternative embodiment of the present invention consists of a method for identifying evidence of a neoplasm in an individual by examining a level of EECP gene expression in a test biological sample obtained from the individual and then comparing the level of EECP gene expression in the test biological sample (e.g. one suspected of a pathological condition) obtained from the individual to a level of EECP gene expression found in a comparable normal biological sample (e.g. one not suspected of a pathological condition) wherein differences in the level of EECP gene products in the test biological sample relative to the normal biological sample are associated with the neoplasm. Preferably, the test biological sample is evaluated by examining the level of EECP mRNA expression or EECP protein expression. In an especially preferred method of the present invention, the neoplasm is a prostate cancer. In an alternative preferred method, the neoplasm is a breast cancer.

A typical preferred embodiment of the present invention consists of a method for detecting a cancer in an individual by examining EECP gene expression in a test biological sample obtained from the individual and then examining the individual for the presence of a factor associated with disrupted tissue structure and/or dysregulated cellular growth where a coincidence of EECP gene expression in the test biological sample obtained from the individual and the presence of the factor associated with disrupted tissue structure and/or dysregulated cellular growth is indicative of the cancer. Various factors associated with dysregulated cellular growth may be utilized as other factors such as the expression of genes associated with dysregulated cellular growth (including mucin, laminin-5, PSA, PSCA and PSM) as well as cytological examinations (see e.g. Pyke et al. *Cancer Res.* 1995 Sep. 15; 55(18):4132-9; Bocking et al., *Anal Quant Cytol.* 6(2):74-88 (1984); Eptsein, *Hum Pathol.* 1995 February; 26(2):223-9 (1995); Thorson et al., *Mod Pathol.* 1998 June; 11(6):543-51; Baisden et al., *Am J Surg Pathol.* 23(8):918-24 91999)). In an especially preferred method of the present invention, the cancer is prostate cancer. In an alternative preferred method, the cancer is breast cancer. In specific embodiments of this method, Southern analysis, Northern analysis, polymerase chain reaction analysis and immunoassay (such as ELISA) are used to examine the level of EECP mRNA expression or the level of EECP protein expression.

Identifying Molecules that Interact with EECP

The EECP protein sequences disclosed herein allow the skilled artisan to identify molecules that interact with them via any one of a variety of art accepted protocols. For example one can utilize a so-called interaction trap systems (also referred to as "two-hybrid assay"). In such systems, the interaction between molecules reconstitutes a transcription factor and directs expression of a reporter gene, the expression of which is then assayed. Typical systems identifying protein-protein interactions in vivo through reconstitution of an eukaryotic transcriptional activator and are disclosed for example in U.S. Pat. Nos. 5,955,280, 5,925,523, 5,846,722 and 6,004,746.

One can screen for molecules that interact with EECP protein sequences by examining a known panel of molecules which are likely to interact with EECP (based on observations with like molecules such as PSA), such as plasma (serum) and semen serpins. Alternatively, one can identify molecules that interact with EECP protein sequences by screening peptide libraries. In such methods, peptides that bind to selected receptor molecules such as EECP are identified by screening libraries that encode a random or controlled collection of amino acids. Peptides having a wide variety of uses, such as therapeutic or diagnostic reagents, can thus be identified without any prior information on the structure of the expected ligand or receptor molecule. Typical peptide libraries and screening methods that can be used to identify molecules that interact with EECP protein sequences are disclosed for example in U.S. Pat. Nos. 5,723,286 and 5,733,731.

Alternatively, cell lines expressing EECP can be used to identify protein-protein interactions mediated by EECP. This possibility can be examined using immunoprecipitation techniques known in the art (see also Hamilton, B. J., et al., 1999, *Biochem. Biophys. Res. Commun.* 261:646-51). Typically EECP protein can be immunoprecipitated from EECP expressing prostate or breast cancer cell lines and/or the secretion products of those cell lines, using anti-EECP antibodies. Additionally, antibodies against His-tag may be used in cell line engineered to express EECP (vectors mentioned above). The immunoprecipitated complex can be examined for protein association by procedures such as Western blotting, $^{35}$S-methionine labeling of proteins, protein microsequencing, silver staining and two-dimensional gel electrophoresis.

Related embodiments of such screening assays include methods for identifying small molecules that interact with EECP. Typical methods are discussed for example in U.S. Pat. No. 5,928,868 and include methods for forming hybrid ligands in which at least one ligand is a small molecule. In an illustrative embodiment, the hybrid ligand is introduced into cells that in turn contain a first and a second expression vector. Each expression vector includes DNA for expressing a hybrid protein that encodes a target protein linked to a coding sequence for a transcriptional module. The cells further contains a reporter gene, the expression of which is conditioned on the proximity of the first and second hybrid proteins to each other, an event that occurs only if the hybrid ligand binds to target sites on both hybrid proteins. Those cells that express the reporter gene are then selected and the unknown small molecule or the unknown hybrid protein is identified.

A typical embodiment of this invention consists of a method of screening for a molecule that interacts with a EECP amino acid sequence shown in FIG. 2, comprising the steps of contacting a population of molecules with the EECP amino acid sequence, allowing the population of molecules and the EECP amino acid sequence to interact under conditions that facilitate an interaction, determining the presence of a molecule that interacts with the EECP amino acid sequence and then separating molecules that do not interact with the EECP amino acid sequence from molecules that interact with the EECP amino acid sequence. In a specific embodiment, the method further includes purifying a molecule that interacts with the EECP amino acid sequence. In a preferred embodiment, the EECP amino acid sequence is contacted with a library of peptides.

Kits

The present invention further provides kits for the diagnostic and therapeutic applications described or suggested above. Such kits comprise a carrier means being compartmentalized to receive one or more container means such as vials, tubes, and the like, each of the container means comprising one of the separate elements to be used in the method. For example, one of the container means may equip with a vector which encodes EECP protein. Another container means equips with a probe which is or can be detectably labeled. Such probe can be an antibody (for example, for use in an ELISA assay) or polynucleotide specific for EECP protein or gene/mRNA, respectively. Where the kits utilize nucleic acid hybridization to detect the target nucleic acid, the kits also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kits of the present invention typically comprise a container described above and one or more other containers comprising materials desirable from a commercial and user standpoint, including buffers, diluents, filters, needles, syringes, and package inserts with instructions for use. A tag can be present on the container to indicate that the composition is used for a specific therapy or non-therapeutic application, and can also indicate directions for either in vivo or in vitro use.

EXAMPLES

Example 1

Isolation of cDNA Corresponding to EECP Gene by Cloning and Expression Analysis

Materials and Methods

Cell lines and human tissues (including various prostate cancer cell lines, such as LnCaP, 22RV1, DU145; breast cancer cell lines, such as T47D, MCF7, UACC-812).

All cell lines are maintained in DMEM with 10% fetal calf serum.

Human tissues for RNA and protein analyses are prostate cancer patient-derived.

RNA Isolation:

Tumor tissue and cell lines are homogenized in Trizol reagent (Life Technologies, Gibco BRL) using 10 ml/g tissue or 10 ml/$10^8$ cells to isolate total RNA. PolyA RNA is purified from total RNA using Qiagen's Oligotex mRNA Mini and Midi kits. Total RNA and mRNA are quantified by spectrophotometric analysis (O.D. 260/280 nm) and analyzed by gel electrophoresis.

Differential Display is performed on pooled prostate cancer tumour tissue and corresponding normal tissue according to the GenHunter protocol and as described by Liang et al [Liang, 1998] using 5' primer HAP42 and 3' primer HT11C. Differential bands are isolated, re-amplified with the corresponding primers, verified by agarose gel electrophoresis, and cloned in the pGEMt-easy vector (Promega). Eight colonies per band are expanded in liquid culture. Two microlitres of the cultures are used for PCR, in the same conditions as the amplification, with the pGEME 1 and 2 primers (5'-CGC GGT ACC GGA TCC ATG CAT TGG CGG CCG CGG GAA TTC-3' [SEQ ID No. 7] and 5'-CGC GGT ACC GGA TCC ATG CAT CAT ATG GTC GAC CTG CAG-3' [SEQ ID No. 8], respectively). PCRs are confirmed by agarose gel electrophoresis.

Sequence analysis of the clone with the BLAST search algorithm (www.ncbi.nlm.nih.gov/blast) indicats that it consists of a fragment corresponding to a sequence on the *H. sapiens* Chromosome 16, cosmid clone 352F10 (LANL) (AC005361).

Example 2

Reverse Northern Analysis and Classical Northern Analysis

For detection of positive clones by Reverse Northern hybridisation, the DNA is spotted directly onto nitrocellulose membranes (Hybond N+Amersham) using a 96-well vacuum-driven dot blotting manifold (Biorad) according to the manufacturers instructions. Filters are denaturated (1.5M NaCl, 0.5M NaOH) and neutralized (1.5M NaCl, 0.5M Tris-HCl pH 7.2, 0.001M EDTA) followed by UV crosslinking. Due to the limiting quantity of patient RNA, the SMART cDNA synthesis system from Clontech is used to reverse transcribe and amplify total RNA to be used as a probe. The first strand, synthesised with 0.2 ug of total RNA, is amplified for a controlled number of cycles, to ensure linearity. For each group of clones probed, the labelling is performed with 100 ng of SMART cDNA and the mixture of primers are those that had generated the subset of clones in the original Differential Display, in this case HAP42 and HT11C. Probes are purified through Sephadex G50 columns (Biorad). The filters are hybridised in 10% dextran sulphate/0.1% SDS/10 mM NaCl overnight at 65° C., washed to a stringency of 0.2×SSC/0.1% SDS at 65° C. and exposed on Biomax film for 3-24 hours at −80° C., and subsequently on Fuji phosphoimage screens for quantification on a Typhoon phosphoimage analyser. Positive clones are then expanded from the original liquid cultures, and plasmid DNA extracted using standard alkaline lysis followed by purification through Nucleospin miniprep columns. Inserts are sequenced. All sequences are analysed with the BLAST algorithm at www.ncbi.nlm.nih.gov/blast.

Classical Northern analysis: Total RNA is extracted from tissue samples with Trizol. 20 □g of RNA is subjected to agarose/6% formaldehyde gel electrophoresis then transferred to nylon membranes (Hybond N+, Amersham). Membranes are prehybridised/hybridised in 50% formamide at 42° C. according to the manufacturer's specifications. Probes are generated using the Rediprime system (Amersham). Following hybridisation the filters are washed to a stringency of 0.1×SSPE/0.1% SDS at 50° C. then exposed to X-ray film (Kodak) for an appropriate amount of time.

Example 3

Cloning of Full Length EECP cDNA

The band from Example 1 is isolated and cloned into the pGEMt-easy vector where the clone containing the fragment that had generated the original differential display profile is identified by reverse Northern analysis and classical Northern analysis. The full-length EECP cDNA is then amplified and cloned by 5'/3' RACE PCR from a normal prostate library (Clontech).

The full-length EECP cDNA is made up of four exons and localises to Chromosome 16p12.3 (FIG. 3). An extensive search of publicly available genomic data fails to identify either paralogues or orthologues (>30% identity) of this gene (mouse, rat, *X. laevis*, drosophila and *C. elegans* at www.tigr.org and mouse and rat at www.ensembl.org). EECP has no close homologues in human, and only distant homologues in rat and mouse. Alignment of EECP protein with its closest homologues as identified by protein-protein BLAST is made against the SWISSPROT database at NCBI. EECP protein is aligned with its closest homologues by protein-protein Blast analysis. Rat corresponds to the gene: Rat prostatic spermine-binding protein precursor (SBP) Accession P08723 (BLAST Identities=37/139 (26%), Positives=66/139 (46%), Gaps=4/139 (2%)). Mouse corresponds to the gene: Mouse major prostatic secretory glycoprotein (p25). Accession X06246 (BLAST Identities=34/134 (25%), Positives=60/134 (44%), Gaps=3/134 (2%)). Alignment is performed using the multalin software at prodes.toulouse.inra.fr/multalin/multalin.html.

Example 4

EECP RNA Expression

In situ hybridisation: In situ hybridisations are carried out on paraffin embedded sections taken from prostate tumours and their surrounding tissue and from sections of histologically normal prostate tissue from the same patients. The probes are prepared from the EECP-pGEMTeasy construct and the in situ hybridisations are carried out according to the procedures described in *Niedereither and Dollé*, 1998 *[Niedereither*, 1998].

Multiple-tissue expression array: A Human Multiple Tissue Expression (MTE™) Array 2 (Clontech) is probed according to the manufacturer's instructions. The membrane is probed with full length EECP cDNA labelled ($[^{32}P]$-dCTP) by PCR. Results are quantified using the Typhoon ImageQuant software following overnight exposure to Fuji phosphorimage screens.

Example 5

Characterization of EECP Protein Generation of EECP Polyclonal and Monoclonal Antibodies (FIG. 2)

A putative translation of EECP mRNA indicates four potential in frame starting methionines (FIG. 1), none with clear Kozac consensus sequences flanking. Therefore to assist in determining the correct translation start, three antibodies are generated, one spanning amino acids 19-32, the second spanning amino acids 55-75, and the third spanning amino acids 178-193. These antibodies are first tested on EECP protein produced by transfection of an expression construct into Du145 cells. The transfected EECP protein was constructed to include all four 5' methionines. All the three antibodies easily and specifically have detected the exogenous EECP in Du145 cell lysates, endogenous secreted EECP in conditioned medium, and native EECP from posterior urethral secretion. Thus it is likely that EECP is translated from the first methionine, although there is another possibility that EECP is produced as a shorter form, and the 5' amino acids is cleaved off prior to secretion. The EECP protein determined therefore is a 208 amino acid protein, with a predicted molecular weight of 25 kD. A search for potential domains and functional motifs/fingerprints etc in the sequence does not detect significant homology to known motifs (motif.genome.ad.jp/) apart from an indication of a low level homology to the mannose-binding lectins and the presence of a potential signal peptide.

EECP represents a potential therapeutic target for prostate cancer and breast cancer. As a cell surface associated antigen as well as a secreted protein, it may be a particularly good target for antibody therapy. To explore this possibility and to further identify the EECP protein, monoclonal antibodies directed against GST-EECP fusion protein are prepared. Mouse MAbs are prepared towards the first 30 amino acids, the 50-80 amino acids and the 170-195 amino acids region of the protein. The GST-fusion protein is generated by PCR. The PCR product is inserted into pGEX-4T-3. GST-fusion protein is purified and used to immunize mice.

Mice are immunized with purified GST-EECP and hybridomas are generated. Hybridoma supernatants generating specific antibodies are screened by Western blotting using lysates from Du145 cells transfected with EECP. Subclones are derived by limiting dilution cloning and screened by Western blot. Seven hybridomas were identified that specifically recognize EECP by Western blotting.

Example 6

EECP is released into the medium of prostate and breast cancer cells, and degraded by proteases.

EECP-transfected Du145 cell line; non-transfected Du145, LNCap, 22RV1 and T47D cell lines are selected. Medium from those cell lines are collected. The medium are then analyzed for the presence of EECP protein by immunoprecipitation and Western blotting using anti-EECP MAb. The results show clearly the detection of EECP protein in the medium of those cells (FIG. 6). The amount of EECP present in the medium is directly correlated to the amount of proteases inhibitor added into the medium, which increases with an increased dose of proteases inhibitor.

Example 7

EECP is highly expressed in the basal layer epithelia, and to the lesser extent, the secretory epithelia of normal prostate acini. The expression level decreases significantly in the tumor cells of malignant acini of prostate. More over, the expression levels among the tumor cells are heterogenous.

The expression of EECP in prostate cancer biopsies and surgical samples are examined by immunohistochemical analysis.

Analysis of clinical specimens shows strong staining in the basal layer epithelia of all normal prostate, there is also relatively strong signal appeared at the apical side of the secretory cells (FIG. 8). The prostate tissue staining is specific, since GST-EECP immunogen could competitively inhibit staining of prostate cancer tissue, while GST alone could not. Similar to PSA, EECP protein is found to accumulate within the lumen of the gland and the ductal, indicating that EECP protein is secreted by the secretory epithelia.

Low protein expression is detected in the malignant acini of prostate, when compare with the normal part of the corresponding prostate. Moreover, the expression levels among the tumor cells are heterogenous: about 60% of the cancerous cells lost the expression of EECP.

Analysis of several non-prostate tissues shows no staining in most tissues, including kidney and lung which express some EECP mRNA message. Protein expressions are detected in normal pancreas samples, normal breast tissues, and breast cancer tissues. The staining in normal breast appears primarily in the secretion cells and ductal cells in glands (FIG. 11). The staining in breast cancer is generally more profound than in the normal breast tissues. Significant accumulation of EECP is detected in luminal areas, further providing evidence of the secretion of such protein. Moreover, as illustrated, the tissue architecture is disrupted in breast cancer, which is likely to result in the leakage of EECP into the bloodstream.

Example 8

Observation of EECP Levels in Biological (Plasma/Serum) Samples

To determine whether the level of EECP protein has biological and clinical applicability in prostate and breast cancer, EECP protein expression is monitored in human clinical prostate and breast cancer plasma (serum) samples. The important point is that the expression level of EECP in female is far less than that of normal male, which strongly suggests that the EECP level in blood is mainly related with male genital organs' endo-secretion of EECP. Western blotting analysis of human male serum samples with anti-EECP antibodies demonstrates high expression of the 25 kD EECP full length protein, in serum of "normal" and "BPH (benign prostate hyperplasia)" patients, but not in "prostate cancer" and "prostate cancer with metastasis" (FIG. 10). The loss of EECP in the plasma (serum) of "prostate cancer" and "prostate cancer with metastasis" patients may be the result of degradation, by those large amount of proteases released into the circulation system from the prostate. And this releasing process is because of the disruption of the basement membrane and other tissue structures in tumor tissue. Moreover, there is just "detectable" level of EECP in some of the "metastasis" cases, when compare to the "un-detectable" EECP level in the "prostate cancer" cases. This result proves that the EECP plasma (serum) level may be also used as a marker for prostate cancer prognosis and therapeutic effect of clinical treatment of the prostate cancer. Meanwhile, Western blotting analysis of human female serum samples with anti-EECP antibodies demonstrates extremely low expression level of the 25 kD EECP full length protein in plasma of "normal" cases, but obviously higher in plasma (serum) of "breast cancer" and "breast cancer with metastasis". In contrary to prostate cancer, these accumulations of newly secreted EECP in the plasma (serum) of "breast cancer" and "breast cancer with metastasis" cases are because of lacking of enough quantity of proteases released into the circulation system from the breast cancer tissue. The different levels of EECP between tumor and normal plasma (serum) samples suggest that EECP may be a plasma (serum) diagnostic marker for prostate and breast cancer.

Example 9

Methodologies to Determine the EECP as a Diagnostic and/or Therapeutic Target for Prostate and Breast Cancer A variety of methodologies well known in the art may be used to identify and quantify the EECP protein in clinical fluids of prostate and breast cancer patients, making it as a diagnostic and/or therapeutic target for prostate and breast cancer. For example, one can further develop sensitive ELISA using existing panel of monoclonal antibodies. Such ELISA protocols have been described for example in *Current Protocols In Molecular Biology, Unit* 11, Frederick M. Ausubul et al. eds., 1995. Additionally, one skilled in the art can analyze a spectrum of clinical samples to evaluate EECP expression and complex formation using, for example immunoprecipitation and Western strategies. Such strategies have been described for example in *Current Protocols In Molecular Biology, Unit* 10, Frederick M. Ausubul et al. eds., 1995. Moreover, one can prepare panels of MAbs to different parts of the EECP protein.

In addition, a variety of methodologies well known in the art can be used to examine and identify novel high molecular weight EECP immunoreactive bands in plasma (serum) and semen. For example, one skilled in the art can screen a series of known molecules which are likely to interact with EECP (based on the observations to the similar molecules such as PSA), such as plasma (serum) and semen serpins to identify the formation of EECP complex. Such candidate molecules also include alpha-1-antichymotrypsin (PSA and hK2 complex in plasma), protein C inhibitor (PSA and hK2 complex in semen), alpha-2-macroglobulin, alpha-1-antitrypsin, alpha-2-antiplasmin, anti-thrombin III and other serpins. Alternatively, one can isolate and sequence the binding partner using known protein purification (such as affinity columns) and sequencing techniques.

In addition, a variety of methodologies well known in the art can be used to discover and identify proteolytic activity and substrate specificity of certain proteases specifically target to EECP. In particular, one can examine the effects of EECP polypeptides on in vitro and in vivo tumor growth employing protease assays, using purified or recombinant EECP. In addition, fluorescent peptide substrates may be used to determine the cleavage specificity using techniques known in the art.

In addition, a variety of methodologies well known in the art may be used to examine the in vivo and in vitro effects of anti-EECP MAbs, EECP protein and/or EECP recombinant protein on tumor growth.

Alternatively, one can examine the effects of such molecules on proliferation/invasion/colony growth in vitro, using, for example, the Matrigel assays known in the art as tumor models (see e.g. Bae et al., *Breast Cancer Res. Tret.* 24(3): 241-55 (1993)).

What is claimed is:

1. An isolated polypeptide comprising an antigenic epitope of the amino acid sequence of SEQ ID NO: 3, wherein the isolated polypeptide has a sequence of amino acids at positions 16 to 32, 1 to 30, 50 to 80, or 170 to 200 of SEQ ID NO: 3, and the isolated polypeptide is from 10 to 50 amino acids in length.

2. A method of preparing an antibody against an isolated polypeptide, the method comprising:
   providing a polypeptide containing an antigenic epitope of the amino acid sequence of SEQ ID NO: 3, and
   raising an antibody against the polypeptide,
   wherein the isolated polypeptide has a sequence of amino acids at positions 16 to 32, 1 to 30, 50 to 80, or 170 to 200 of SEQ ID NO: 3, and the isolated polypeptide is from 10 to 50 amino acids in length.

3. The method of claim 2, wherein the antibody is a monoclonal antibody or polyclonal antibody.

4. The isolated polypeptide of claim 1, wherein the isolated polypeptide has a sequence of amino acids at positions 16 to 32 of SEQ ID NO: 3.

5. The isolated polypeptide of claim 1, wherein the isolated polypeptide has a sequence of amino acids at positions 1 to 30 of SEQ ID NO: 3.

6. The isolated polypeptide of claim 1, wherein the isolated polypeptide has a sequence of amino acids at positions 50 to 80 of SEQ ID NO: 3.

7. The isolated polypeptide of claim 1, wherein the isolated polypeptide has a sequence of amino acids at positions 170 to 200 of SEQ ID NO: 3.

8. The method of claim 2, wherein the isolated polypeptide has a sequence of amino acids at positions 16 to 32 of SEQ ID NO: 3.

9. The method of claim 2, wherein the isolated polypeptide has a sequence of amino acids at positions 1 to 30 of SEQ ID NO: 3.

10. The method of claim 2, wherein the isolated polypeptide has a sequence of amino acids at positions 50 to 80 of SEQ ID NO: 3.

11. The method of claim 2, wherein the isolated polypeptide has a sequence of amino acids at positions 170 to 200 of SEQ ID NO: 3.

12. The method of claim 3, wherein the isolated polypeptide has a sequence of amino acids at positions 16 to 32 of SEQ ID NO: 3.

13. The method of claim 3, wherein the isolated polypeptide has a sequence of amino acids at positions 1 to 30 of SEQ ID NO: 3.

14. The method of claim 3, wherein the isolated polypeptide has a sequence of amino acids at positions 50 to 80 of SEQ ID NO: 3.

15. The method of claim 3, wherein the isolated polypeptide has a sequence of amino acids at positions 170 to 200 of SEQ ID NO: 3.

* * * * *